(12) United States Patent
Taber

(10) Patent No.: US 9,883,897 B2
(45) Date of Patent: Feb. 6, 2018

(54) METHOD AND APPARATUS FOR A COMPRESSING PLATE

(71) Applicant: BioMedical Enterprises, Inc., San Antonio, TX (US)

(72) Inventor: Joseph H. Taber, San Antonio, TX (US)

(73) Assignee: BioMedical Enterprises, Inc., San Antonio, TX (US)

( * ) Notice: Subject to any disclaimer, the term of this patent is extended or adjusted under 35 U.S.C. 154(b) by 343 days.

(21) Appl. No.: 14/861,245

(22) Filed: Sep. 22, 2015

(65) Prior Publication Data

US 2016/0089190 A1 Mar. 31, 2016

Related U.S. Application Data

(60) Provisional application No. 62/055,175, filed on Sep. 25, 2014.

(51) Int. Cl.
*A61B 17/80* (2006.01)
*A61B 17/17* (2006.01)
*A61B 17/16* (2006.01)
*A61B 17/00* (2006.01)

(52) U.S. Cl.
CPC ........ *A61B 17/808* (2013.01); *A61B 17/1615* (2013.01); *A61B 17/1728* (2013.01); *A61B 17/80* (2013.01); *A61B 2017/00867* (2013.01); *A61B 2017/00871* (2013.01)

(58) Field of Classification Search
None
See application file for complete search history.

(56) References Cited

U.S. PATENT DOCUMENTS

| | | |
|---|---|---|
| 3,779,240 A | 12/1973 | Kondo |
| 3,866,607 A | 2/1975 | Forsythe |
| 3,939,828 A | 2/1976 | Mohr et al. |
| 4,408,601 A | 10/1983 | Wenk |
| 4,513,744 A | 4/1985 | Klaue |
| 5,634,926 A | 6/1997 | Jobe |
| 5,779,707 A | 7/1998 | Bertholet et al. |
| 5,785,713 A | 7/1998 | Jobe |
| 6,001,110 A | 12/1999 | Adams |
| 6,093,188 A | 7/2000 | Murray |
| 6,187,009 B1 | 2/2001 | Herzog et al. |
| 6,325,805 B1 | 12/2001 | Ogilvie et al. |
| 6,773,437 B2 | 8/2004 | Ogilvie et al. |
| 7,115,129 B2 | 10/2006 | Heggeness |
| 7,857,838 B2 | 12/2010 | Orbay |
| 7,867,265 B2 | 1/2011 | Beutter |
| 7,931,679 B2 | 4/2011 | Heggeness |
| 7,931,680 B2 | 4/2011 | Myerson |
| 8,083,781 B2 | 12/2011 | Reimels |

(Continued)

*Primary Examiner* — Christopher Beccia
(74) *Attorney, Agent, or Firm* — Christopher L. Makay

(57) ABSTRACT

An orthopedic bone plate constructed from shape memory material provides the ability to move from an open shape to a compressed shape and create compression on two bones or bone fragments to encourage healing. The plate may be any umber of shapes, with two or more screws anchoring the plate to bone. The plate is affixed to bone in a sequence of steps that involve first placing the plate on an insertion tool, attaching drill guide tubes, placing the plate over bone, drilling holes in bone, and then attaching the plate to the bone via screws. The insertion tool can then be removed at the surgeon's convenience allowing compression on the two bones.

13 Claims, 42 Drawing Sheets

(56) References Cited

U.S. PATENT DOCUMENTS

| | | |
|---|---|---|
| 8,118,952 B2 | 2/2012 | Gall |
| 8,167,918 B2 | 5/2012 | Strnad |
| 8,172,886 B2 | 5/2012 | Castaneda et al. |
| 8,226,693 B2 | 7/2012 | Reimels |
| 8,231,625 B2 | 7/2012 | Graham |
| 8,257,403 B2 | 9/2012 | Den Hartog |
| 8,348,980 B2 | 1/2013 | Prasad |
| 8,535,355 B2 | 9/2013 | Prasad |
| 8,574,270 B2 | 11/2013 | Hess |
| 8,585,742 B2 | 11/2013 | Windolf |
| 8,685,067 B2 | 4/2014 | King |
| 8,728,127 B2 | 5/2014 | Stewart |
| 8,828,063 B2 | 9/2014 | Blitz |
| 8,882,815 B2 | 11/2014 | Bottlang |
| 8,940,026 B2 | 1/2015 | Hilse |
| 8,974,504 B2 | 3/2015 | Hess et al. |
| 8,986,353 B2 | 3/2015 | Johnson |
| 9,005,255 B2 | 4/2015 | Lewis |
| 9,005,257 B2 | 4/2015 | Sun |
| 2004/0034354 A1 | 2/2004 | Paul |
| 2004/0260306 A1 | 12/2004 | Fallin et al. |
| 2005/0085812 A1 | 4/2005 | Sherman et al. |
| 2005/0085814 A1 | 4/2005 | Sherman et al. |
| 2005/0187555 A1 | 8/2005 | Biedermann et al. |
| 2005/0273108 A1 | 12/2005 | Groiso |
| 2006/0235405 A1 | 10/2006 | Hawkes |
| 2006/0293670 A1 | 12/2006 | Smisson, III et al. |
| 2007/0225715 A1 | 9/2007 | Deffenbaugh et al. |
| 2008/0097443 A1 | 4/2008 | Campbell |
| 2009/0062800 A1 | 3/2009 | Shano |
| 2009/0275947 A1 | 11/2009 | Graham et al. |
| 2011/0178555 A1 | 7/2011 | Heggeness |
| 2013/0026206 A1 | 1/2013 | Fox |
| 2013/0026207 A1 | 1/2013 | Fox |
| 2013/0030437 A1 | 1/2013 | Fox |
| 2013/0030438 A1 | 1/2013 | Fox |
| 2013/0206815 A1 | 8/2013 | Fox |
| 2013/0231667 A1 | 9/2013 | Taylor et al. |

METHOD AND APPARATUS FOR A COMPRESSING PLATE

BACKGROUND OF THE INVENTION

1. Field of the Invention

The present invention relates to compressing plates and more particularly but not by way of limitation to a method and apparatus for the use of compressing plates to assist in osteosynthesis.

2. Description of the Related Art

Wire, staple, and plate fixation of bone have been used clinically for decades. In the last 20 years or so, nickel-titanium and shape memory materials have been used in orthopedics for their shape changing and superelastic properties. Shape memory devices feature a martensitic and austenitic form, in which the addition of energy in the form of heat transforms the device from a temporary mart site state to a final austenite state at a defined temperature. The heat for transformation generally is categorized as being (1) room temperature activated (i.e. superelastic), (2) body temperature activated (i.e. body temperature), and (3) above body temperature activated (i.e. heated). The use of a shape memory plate, capable of transforming from a preliminary shape to a compressed final shape, presents unique challenges. If the plate is superelastic, then the plate is inclined to immediately transform at room temperature, making implantation and the use of screws difficult for a surgeon. If the plate is body temperature or heated, then the surgeon has to rely on either body heat, which is reduced during surgery due to the open wound, or an external heating source to transform the plate. For various reasons, many surgeons would prefer a superelastic shape memory plate.

Accordingly, an apparatus and a method of surgical use for a shape memory plate that restrains the plate in an open position while screws are attached and then releases the plate to compress the bones and assist with osteosynthesis would provide an improvement in compressing plate surgeries.

SUMMARY OF THE INVENTION

In accordance with a fixation system of the present invention, a plate is movable between an implantation shape and an insertion shape such that the plate creates compression between a first bone and a second bone. The plate includes a body portion having a central axis. A first body section extends from the body portion and terminates in a first end portion, and a second body section extends from the body portion and terminates in a second end portion. The first body section and the second body section rotate about the central axis of the body portion during movement of the plate between the insertion shape and the implantation shape. The first end portion and the second end portion have a first linear distance when the plate is in the implantation shape and a second linear distance when the plate is in the insertion shape. The first linear distance is less than the second linear distance such that plate creates compression during movement of the plate from the insertion shape toward the implantation shape. First and second screw holes are disposed in the first body section, and third and fourth screw holes disposed in the second body section.

An insertion tool holds the plate in the insertion shape and allows locating of the plate in the insertion shape for affixing with the first bone and the second bone. Release of the plate from the insertion tool after affixation of the plate with the first bone and the second bone allows the plate to move from its insertion shape to its implantation shape, thereby compressing the first bone with the second bone. The insertion tool includes a platform that mates with the body portion and the first and second body sections of the plate. The platform includes a first slot that aligns with the first and second screw holes of the plate and a second slot that aligns with the third and fourth screw holes of the plate. The insertion tool further includes a shaft secured with the platform.

First and second drill guide tubes, each including an inner cannulation adapted to receive a locating pin or a drill bit, insert within the first slot of the platform and mate respectively with the first and second screw holes of the plate. Third and fourth drill guide tubes, each including an inner cannulation adapted to receive a locating pin or a drill bit, insert within the second slot of the platform and mate respectively with the third and fourth screw holes of the plate such that the platform holds the plate in the insertion shape. The first, second, third, and fourth screw holes of the plate include threads that engage a respective one of the first, second, third, and fourth drill guide tubes to maintain the first, second, third, and fourth drill guide tubes secured to the plate with the platform therebetween. After removal of the first, second, third, and fourth drill guide tubes, the threads engage a screw inserted into the first or second bones to maintain the plate secured with the first and second bones.

First and second locating pins temporarily anchor the plate with the first and second bones. The first locating pin inserts through one of the first and second drill guide tubes and one of the first and second screw holes of the plate such that the first locating pin retains the plate at the first bone. The second locating pin inserts through one of the third and fourth drill guide tubes and one of the third and fourth screw holes of the plate such that the second locating pin retains the plate at the second bone.

A drill bit is used to create a hole in the first and second bone. The drill bit inserts through one of the first, second, third, and fourth drill guide tubes and through one of the first and second screw hole of the plate to produce a drill hole in one of the first and second bones.

A package may receive therein the plate coupled with the insertion tool such that the insertion tool retains the plate in its insertion position. The package maintains the plate and the insertion tool sterile after sterilization of the fixation system. The package may receive therein the plate coupled with the insertion tool such that the insertion tool retains the plate in its insertion position and the first, second, third, and fourth drill guide tubes coupled with the plate. The package maintains the plate, the insertion tool, and the first, second, third, and fourth drill guide tubes sterile after sterilization of the fixation system.

In a method for affixing a first bone with a second bone, the fixation system of the present invention is placed onto the first and second bones. A first locating pin is inserted through the first drill guide tube and into the first bone and a second locating pin is inserted through the fourth drill guide tube and into the second bone to retain the fixation system on the first and second bones. A drill bit is inserted through the second drill guide tube to drill a hole into the first bone, and the drill bit is inserted through the third drill guide tube to drill a hole into the second bone. The second drill guide tube is removed from the plate, and a first screw is inserted through the insertion tool to secure the first screw with the plate and the first bone. The third drill guide tube is removed from the plate, and a second screw is inserted through the insertion tool to secure the second screw with the plate and the second bone. The first locating pin is removed from the first drill guide tube, and the second locating pin is removed from the fourth drill guide tube. The drill bit is inserted through the first drill guide tube to drill a hole into the first bone, and the drill bit is inserted through the fourth drill guide tube to drill a hole into the second bone. The first and fourth drill guide tubes are removed from the plate, and the insertion tool is decoupled from the plate. A third screw is secured with the plate and the first bone, and a fourth screw is secured with the plate and the second bone. The plate moves from the insertion shape to the implantation shape, thereby compressing the first bone and the second bone.

In a method for affixing a first bone with a second bone, a first fixation system is placed onto the first and second bones. A first locating pin is inserted through the first drill guide tube of the first fixation system and into the first bone, and a second locating pin is inserted through the fourth drill guide tube of the first fixation system and into the second bone to retain the first fixation system on the first and second bones. A drill bit is inserted through the second drill guide tube of the first fixation system to drill a hole into the first bone. The drill bit is inserted through the third drill guide tube of the first fixation system to drill a hole into the second bone. The second drill guide tube of the first fixation system is removed from the plate of the first fixation system. A first screw is inserted through the insertion tool of the first fixation system and secured with the plate of the first fixation system and the first bone. The third drill guide tube of the first fixation system is removed from the plate of the first fixation system. A second screw is inserted through the insertion tool of the first fixation system and secured with the plate of the first fixation system and the second bone. The first locating pin is removed from the first drill guide tube of the first fixation system, and the second locating pin is removed from the fourth drill guide tube of the first fixation system. The drill bit is inserted through the first drill guide tube of the first fixation system to drill a hole into the first bone. The drill bit is inserted through the fourth drill guide tube of the first fixation system to drill a hole into the second bone. The first and fourth drill guide tubes of the first fixation system are removed from the plate of the first fixation system. A third screw is secured with the plate of the first fixation system and the first bone, and a fourth screw is secured with the plate of the first fixation system and the second bone.

The second fixation system is placed onto the first and second bones. A first locating pin is inserted through the first drill guide tube of the second fixation system and into the first bone, and a second locating pill is inserted through the fourth drill guide tube of the second fixation system and into the second bone to retain the second fixation system on the first and second bones. A drill bit is inserted through the second drill guide tube of the second fixation system to drill a hole into the first bone. The drill bit is inserted through the third drill guide tube of the second fixation system to drill a hole into the second bone. The second drill guide tube of the second fixation system is removed from the plate of the second fixation system. A first screw is inserted through the insertion tool of the second fixation system and secured with the plate of the second fixation system and the first bone. The third drill guide tube of the second fixation system is removed from the plate of the second fixation system. A second screw is inserted through the insertion tool of the second fixation system and secured with the plate of the second fixation system and the second bone. The first locating pin is removed from the first drill guide tube of the second fixation system, and the second locating pin is removed from the fourth drill guide tube of the second fixation system. The drill bit is inserted through the first drill guide tube of the second fixation system to drill a hole into the first bone. The drill bit is inserted through the fourth drill guide tube of the second fixation system to drill a hole into the second bone. The first and fourth drill guide tubes of the second fixation system are removed from the plate of the second fixation system. A third screw is secured with the plate of the second fixation system and the first bone, and a fourth screw is secured with the plate of the second fixation system and the second bone. The insertion tool of the first fixation system is decoupled from the plate of the first fixation system, and the insertion tool of the second fixation system is decoupled from the plate of the second fixation system. The plates of the first and second fixation systems move from the insertion shape to the implantation shape, thereby compressing the first bone and the second bone.

DETAILED DESCRIPTION OF THE PREFERRED EMBODIMENTS

Figure 1:
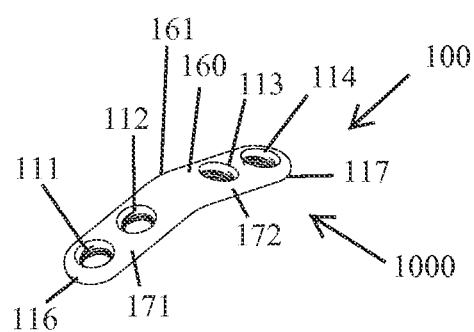
FIG. 1 is a perspective view of a shape memory plate in a first shape according to a first embodiment.
Figure 2:
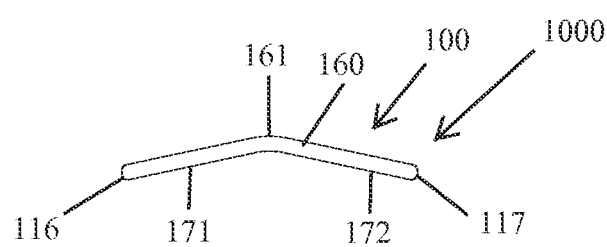
FIG. 2 is a front view of the shape memory plate in a first shape.
Figure 3:
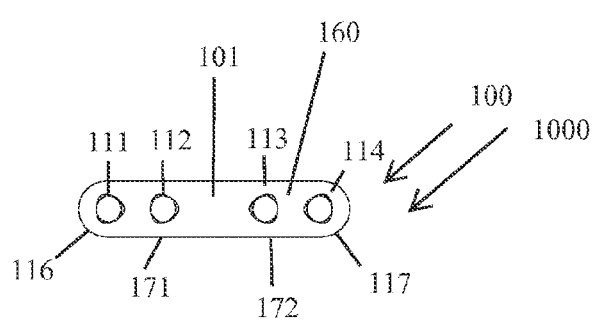
FIG. 3 is a bottom view of the shape memory plate in a first shape.
Figure 4:
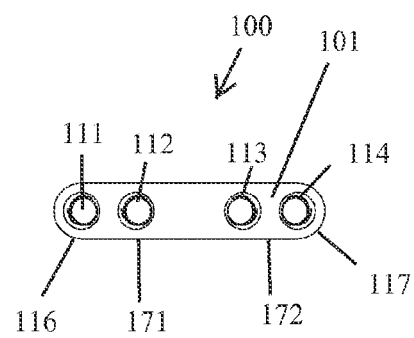
FIG. 4 is a top view of the shape memory plate in a first shape.
Figure 5:
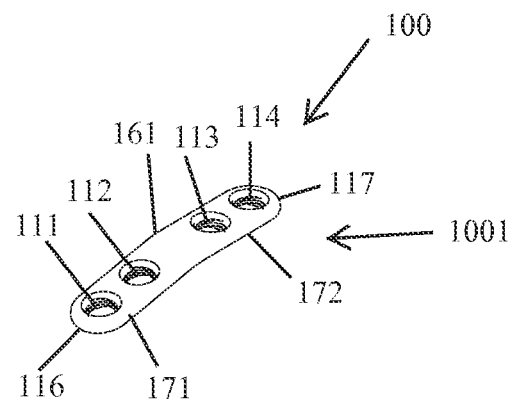
FIG. 5 is a perspective view of the shape memory plate in a second shape.
Figure 6:
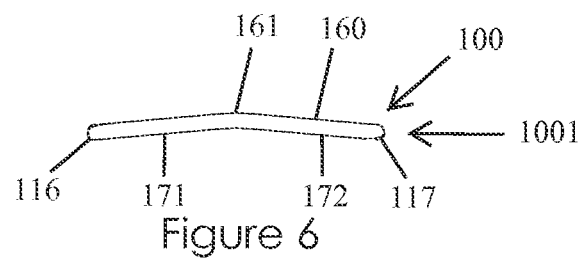
FIG. 6 is a front view of the shape memory plate in a second shape.

As required, a detailed embodiment of the present invention is disclosed herein; however, it is to be understood that the disclosed embodiment is merely exemplary of the invention, which may be embodied in various forms. It is further to be understood that the figures are not necessarily to scale, and some features may be exaggerated to show details of particular components or steps.

FIGS. 1-6 illustrate an orthopedic plate 100 according to a first embodiment. The plate 100 can be fabricated from a shape memory material such as nitinol (nickel-titanium), or any other elastic material capable of deforming and rebounding to an original shape. The plate 100 includes a body portion 160, screw holes 111-114, a central axis 161, a first body section 171 terminating in an end portion 116, and a second body section 1172 terminating in an end portion 117. One of ordinary skill in the art will recognize that the plate 100 may include more or less screw holes depending upon the type of surgery. The screw holes 111-114, or any number of screw holes, can be smooth, tapered, or threaded as necessary to engage a screw. In the first embodiment, the screw holes 111-114 are shown with threads. The plate 100 moves between a first implanted shape 1000 illustrated in FIGS. 1-4 and a second insertion shape 1001 illustrated in FIGS. 5 and 6. The first implanted shape 1000 is the original fabrication shape of the plate 100. In moving between the first implanted shape 1000 and the second insertion shape 1001, the end portions 116 and 117 move between a first position 1100 and a second position 1101.

In the first embodiment, the plate 100 operates to create compression between first and second bones or bone parts. In the first implanted shape 1000, the end portions 116 and 117 in their first positions 1100 have a first linear distance therebetween. In the second insertion shape 1001, the end portions 116 and 117 in their second position 1101 have a second linear distance therebetween. The second linear distance of the second insertion shape 1001 is greater than the first linear distance of the first implanted shape 1000.

In moving from the second insertion shape 1001 to the first implanted shape 1000, the first body section 171 and the second body section 171 pivot about the central axis 161 such that the end portions 116 and 117 move from their second position 1101 to their first position 1100. As a result, the end portions 116 and 117 move from their second linear distance to their first linear distance thereby creating compression between first and second bones or bone parts. One of ordinary skill in the art will recognize that the linear distance traveled by the end portions 116 and 117 from the second position 1101 to the first position 1100 can be any amount that creates a desired level of compression.

The plate 100 begins in the first implanted shape 1000 and through application of an external force, the plate is moved from its first implanted shape 1000 to its second insertion shape 1001. In particular, the application of an external force causes the first body section 171 and the second body section 171 to pivot about the central axis 161 such that the end portions 116 and 117 move from their first position 1100 to their second position 1101.

The plate 100 may change shape from the second shape 1001 to the first implanted shape 1000 through the application of energy delivered from an external source such as room temperature, body temperature, or an external energy device. In the first embodiment however, the plate 100 is superelastic in that the plate 100 internally stores mechanical energy in its metallic structure when moved from its original first implanted shape 1000 to its second insertion shape 1100. The mechanical energy remains stored within the plate 100 as the plate 100 is held in the second shape 1001. Upon release the mechanical energy is recovered when the plate 100 moves from the second shape 1001 to the first implanted shape 1000. In moving from the from the second shape 1000 to the first implanted shape 1000, the end portions 116 and 117 move from the second position 1101 to the first position 1100. In particular, in moving from the second position 1101 to the first position 1100, the end portions 116 and 117 move from their second linear distance to their first linear distance, thus reducing the distance between the end portions 116 and 117. Furthermore, in moving between the second shape 1001 and the first implanted shape 1000, the screw holes 111-114 can remain circular or change shape if it is desired that they bind upon screws.

Figure 7:
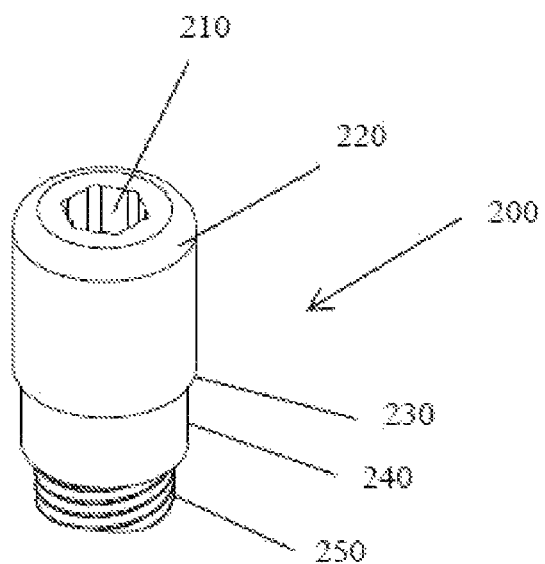
FIG. 7 is a perspective view of a drill guide tube.
Figure 8:
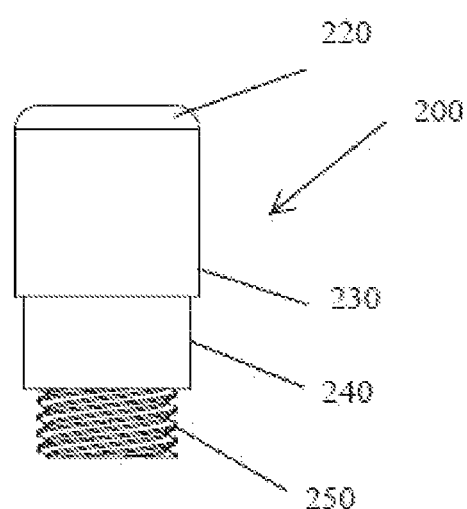
FIG. 8 is a front view of the drill guide tube.

FIGS. 7 and 8 illustrate a drill guide tube 200. The drill guide tube 200 can be made from metal or plate, and has an inner cannulation of diameter 210 and an outer surface 220. A shoulder 230 is a location where a large outer surface 220 reduces to a new small outer surface 240 of smaller diameter. The screw threads 250 extend from the small outer surface 240, and are of the same thread characteristics needed to mate with the screw holes 111-114 of the plate 100.

Figure 9:
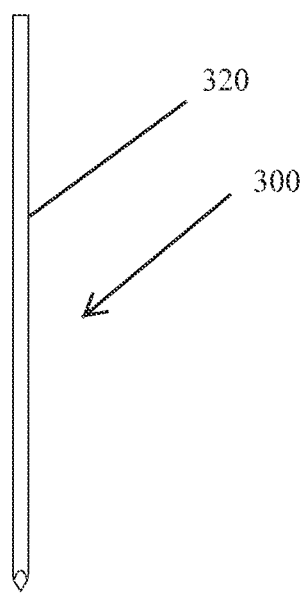
FIG. 9 is a perspective view of a locating pin.

FIG. 9 illustrates a locating pin 300. The locating pin 300 can be manufactured of any material; in the first embodiment, it is made from medical grade metal. A shank 320 of the locating pin 300 is of a diameter that will fit into the inner cannulation 210 of the drill guide tube 200. The locating pin 300 holds the plate 100 in a desired position so that a surgeon can drill holes into the patient's bone.

Figure 10:
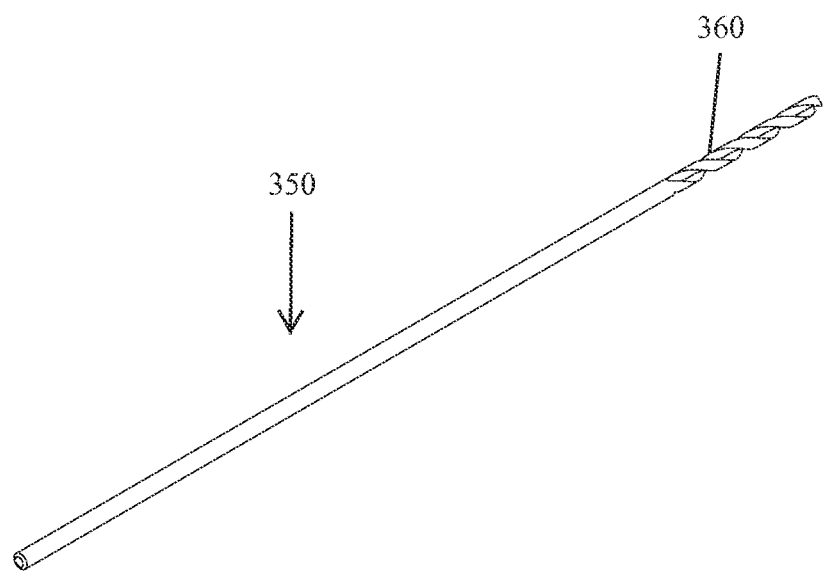
FIG. 10 is a perspective view of a drill bit.

FIG. 10 illustrates a drill bit 350. The drill bit 350 has cutting flutes 360 for cutting through bone and can be manufactured of any material; in the first embodiment, it is made from medical grade metal. The drill bit 350 is of a diameter that will fit into the inner cannulation 210 of the drill guide tube 200. The drill bit 350 may include sizing lines to define certain depths for the drilling of a pilot hole.

Figure 11:
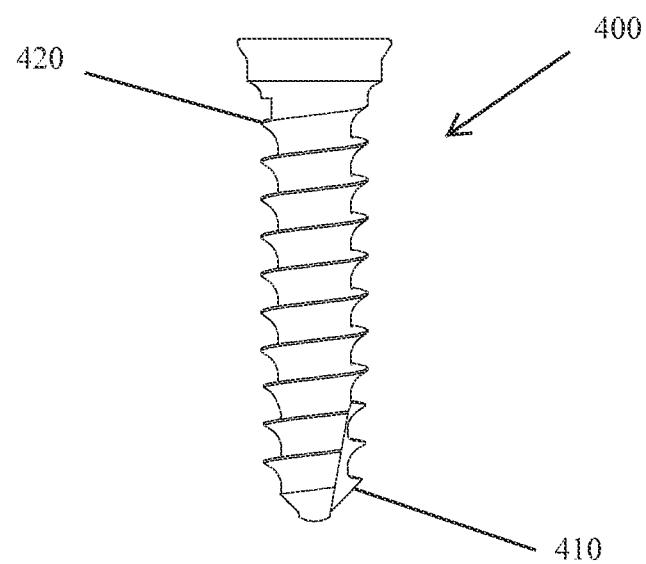
FIG. 11 is a front view of a screw.

FIG. 11 illustrates a screw 400 designed to attach the plate 100 to a bone. In the first embodiment, the screw 400 has two threaded sections, shank threads 410 and head threads 420. The shank threads 410 are designed to engage bone once inserted into a pilot hole created by the drill bit 350. There is any number of thread characteristics related to pitch, diameter, and threads per inch that will accomplish this purpose. The head threads 420 are designed to engage the screw holes 111-114 of the plate 100.

Figure 12:
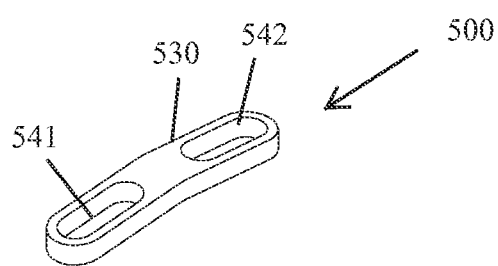
FIG. 12 is a perspective view of an insertion tool.
Figure 13:
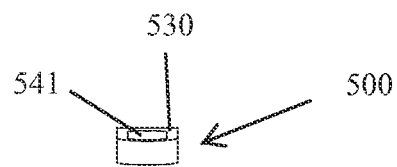
FIGS. 13 and 14 are side views of the insertion tool.
Figure 14:
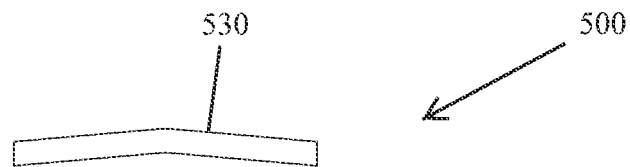
Figure 15:
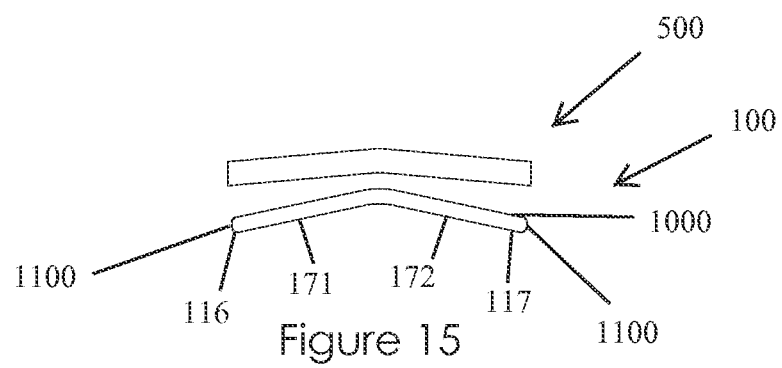
FIG. 15 is a front view of the insertion tool and the shape memory plate in the first position
Figure 16:
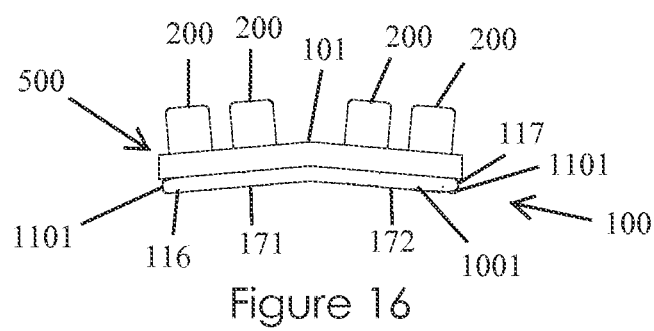
FIG. 16 is a front view of the insertion tool and the shape memory plate in the second shape secured to the insertion tool using the drill guide tubes.
Figure 17:
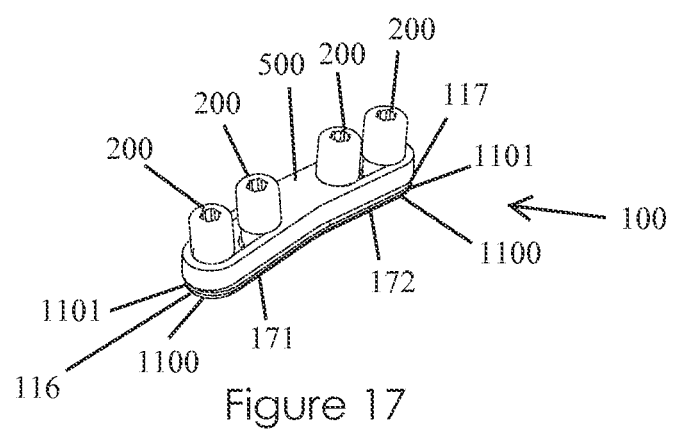
FIG. 17 is a perspective view of the insertion tool and the shape memory plate in the second shape secured to the insertion tool using the drill guide tubes.
Figure 18:
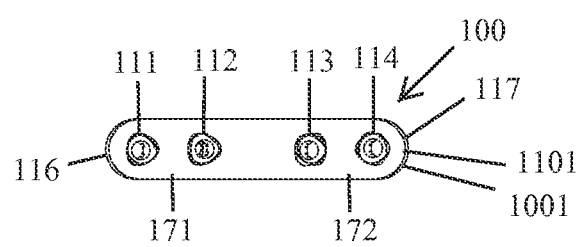
FIG. 18 is a bottom view of the insertion tool and the shape memory plate in the second shape secured to the insertion tool using the drill guide tubes.

FIGS. 12-14 illustrate an insertion tool 500. The insertion tool 500 consists of platform 530 that includes drill guide slots 541 and 542. The platform 530 is a solid material such as metal or plastic, designed to space the drill guide slots 541 and 542 to the proper separation distance, as well as retain the plate 100 in the second shape 1001. Accordingly, the drill guide slot 541 aligns with the first body section 171 and screws holes 111 and 112 and the drill guide slot 542 aligns with the second body section 172 and the screw holes 113 and 114.

FIGS. 15-18 illustrate an assembly showing the plate 100, the four drill guide tubes 200, and the insertion tool 500. The plate 100 begins in the first implanted shape 1000 and ends in the second shape 1001 upon assembly with the insertion tool 500. The body portion 160 of the plate 100 mates with the platform 530 of the insertion tool 500. After mating with the platform 530, the drill guide tubes 200 are used secure the plate 100 to the platform 530 of the insertion tool 500. In particular, the small outer surface 240 of the drill guide tubes 200 pass through the drill guide slots 541 and 542 that are located on the platform 530 of the insertion tool 500. The screw threads 250 on the drill guide tubes 200 are screwed into the screw holes 111-114 of the plate 100 until the shoulders 230 of the drill guide tubes 200 abut the platform 530 of the insertion tool 500. In the first embodiment, the drill guide tubes 200 screw into the screw holes 112 and 113 and then into the screw holes 111 and 114 thereby securing the plate 100 to the platform 530 of the insertion tool 500. Once secured to the platform 530 of the insertion tool 500, the drill guide tubes 200 maintain the plate 100 in its second shape 1001. In mating the plate 100 with the platform 530, it may be necessary to first mechanically deform the plate 100 from the first shape implanted 1000 to the second shape 1001 before securing the plate 100 with the platform 530. Alternatively, securing the plate 100 with the platform 530 using the drill guide tubes 200 may facilitate the mechanical deformation of the plate 100 from the first implanted shape 1000 to the second shape 1001 without prior mechanical deformation.

Figure 19:
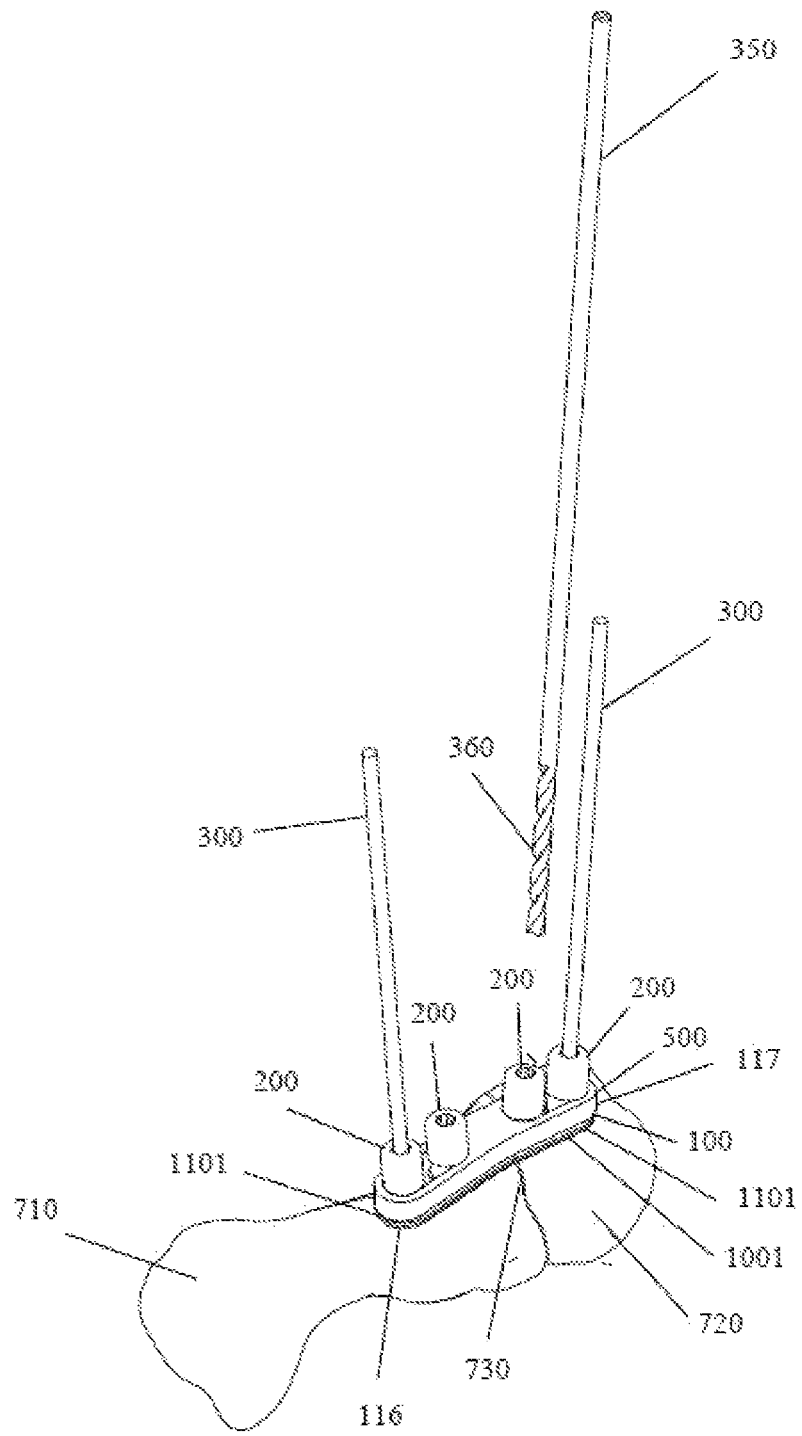
FIGS. 19-24 are perspective views illustrating the use of the insertion tool in affixing the shape memory plate to a first bone and a second bone.

FIGS. 19-26 illustrate a method of use for a shape memory plate 100 to fixate two bones or bone fragments in a surgery. The surgical procedure begins with the surgeon trying to fixate a first bone 710 and a second bone 720. As illustrated in FIG. 19, the plate 100 resides in the second shape 1001 as a result of the securing of the plate 100 to the insertion tool 500 using the drill guide tubes 200 as described above. Using the insertion tool 500, the plate 100 is positioned on top of a bone fusion interface 730, which lies between the first bone 710 and the second bone 720. The screw holes 111-114 of the plate 100 are positioned so that the screw holes 111 and 112 are over the first bone 710 and screw holes 113 and 114 are over the second bone 720.

After positioning the plate 100, the surgeon uses two locating pins 300 to temporarily anchor the plate 100 in place. Specifically, the surgeon places the locating pins 300 through the drill guide tubes 200, through the platform 530 of the insertion tool 500, through respective screw holes 111 and 114 of the plate 100, and then into respective first and second bones 710 and 720. Once the plate 100 is anchored in place, the surgeon drills pilot holes into the first and second bones 710 and 720 using the drill bit 350. Specifically, the surgeon drills pilot holes through the drill guide tubes 200, through the platform 530 of the insertion tool 500, through respective screw holes 112 and 113 of the plate 100, and then into respective first and second bones 710 and 720. The surgeon can use any sizing lines located on the drill bit 350 to assess the depth of a screw 400 to anchor the plate 100.

Figure 20:
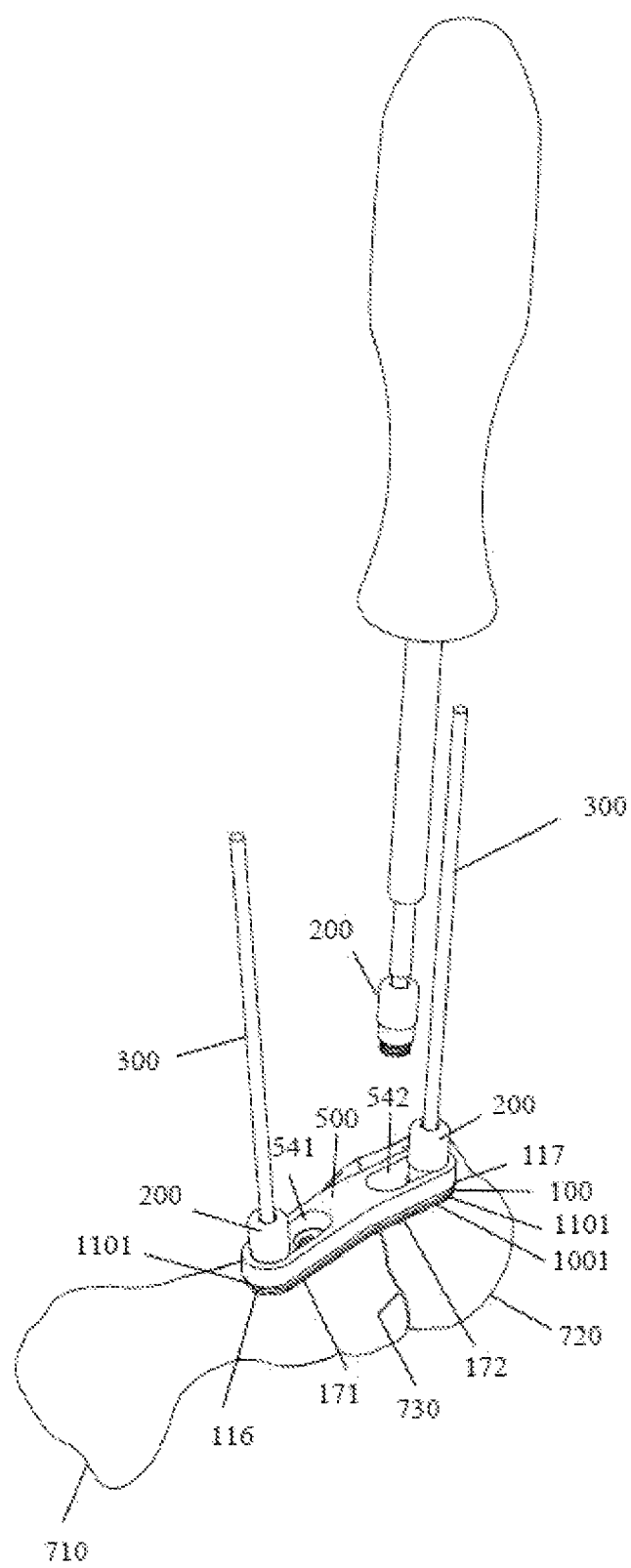
Figure 21:
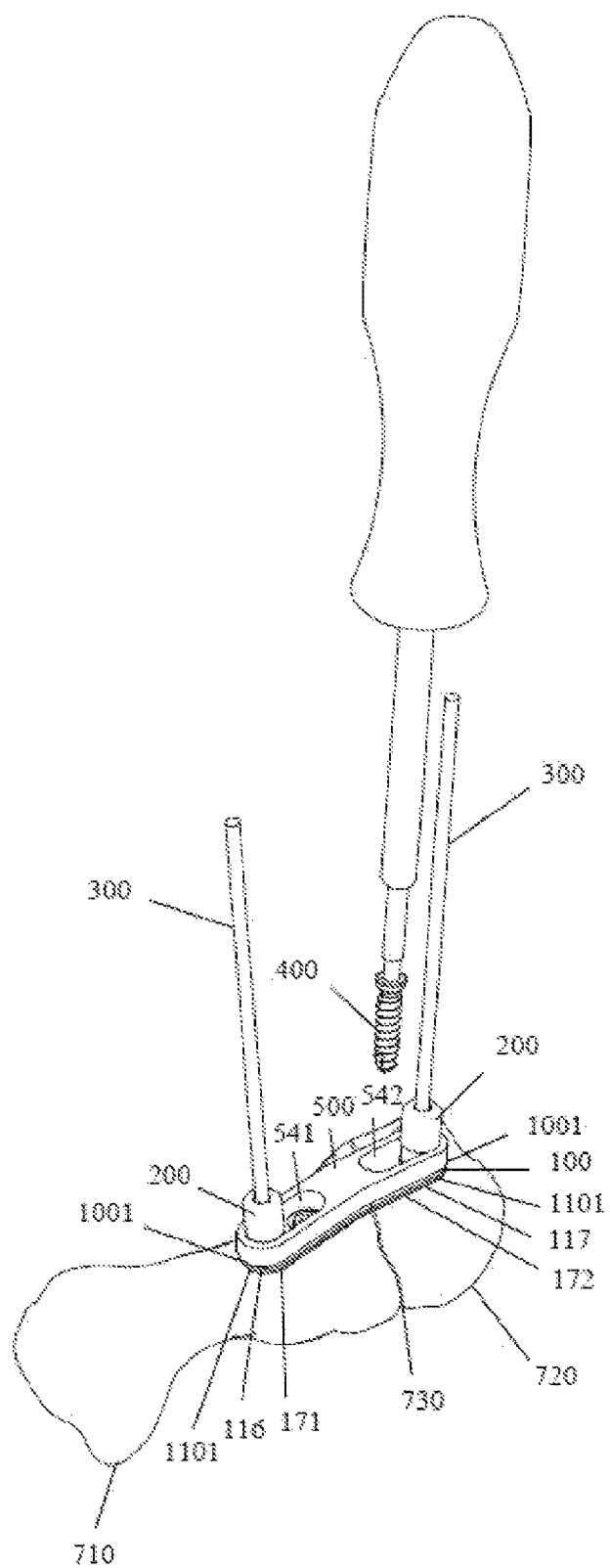

At this time, the surgeon is ready to screw the plate 100 to the first and second bones 710 and 720. As illustrated in FIG. 20, the drill guide tubes 200 corresponding to the screw holes 112 and 113 have been removed from the plate 100 and the platform 530 of the insertion tool 500. Referring to FIG. 21, the surgeon then inserts first and second screws 400 into the screw holes 112 and 113 of the plate 100 To reach the screw holes 112 and 113, the first and second screws 400 pass through the screw slots 541 and 542 of the insertion tool 500. The head threads 420 of the screws 400 mate with the screw hole 112 and 113 of the plate 100 and the shank threads 410 of the screws 400 are screwed into the first bone 710 and the second bone 720.

Figure 22:
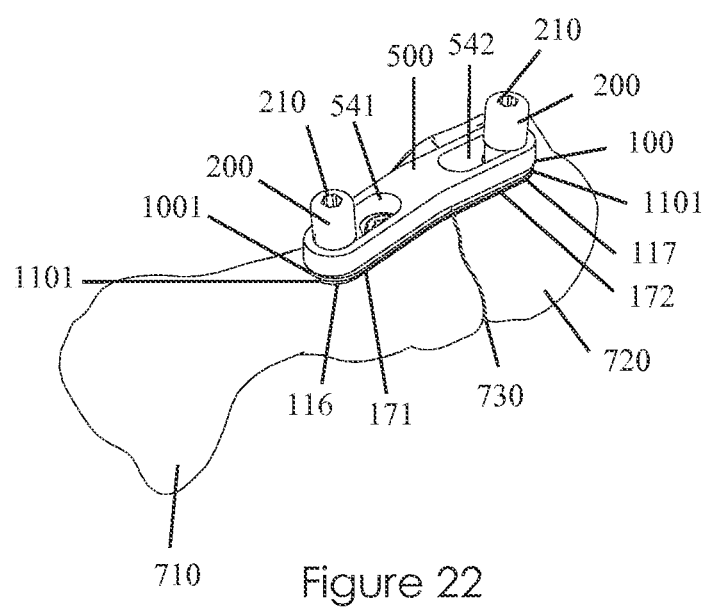
Figure 23:
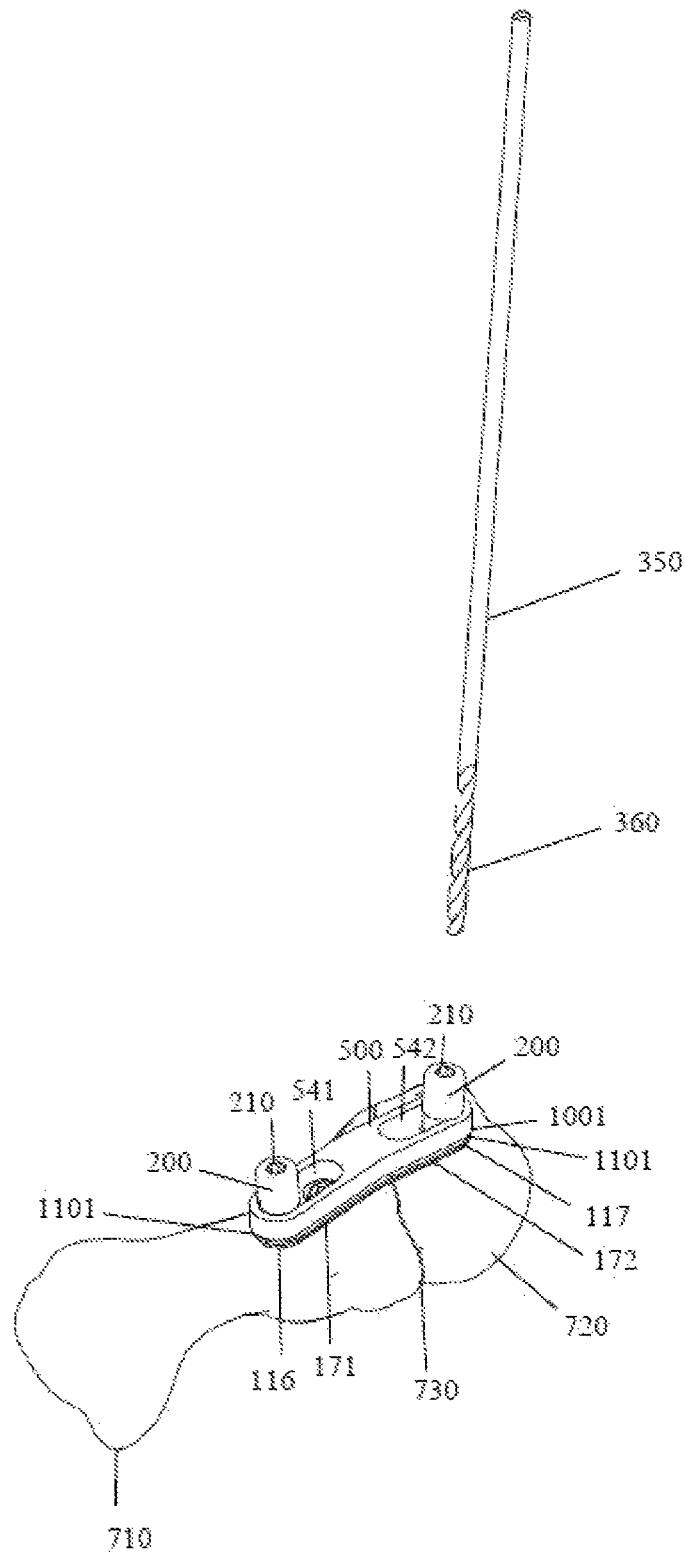
Figure 24:
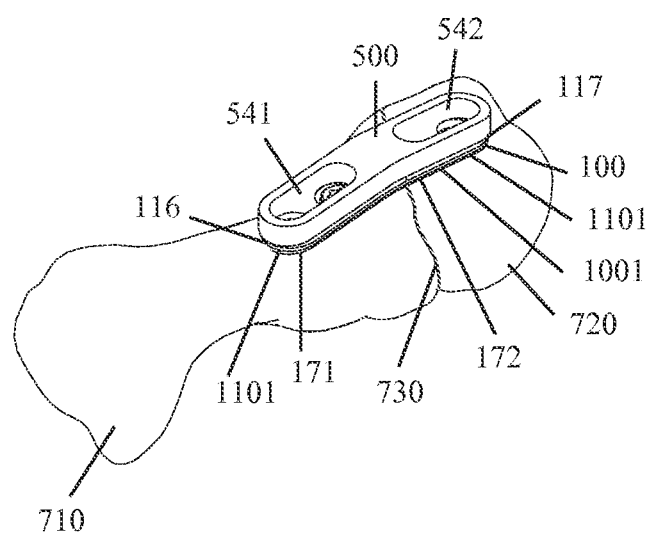
Figure 25:
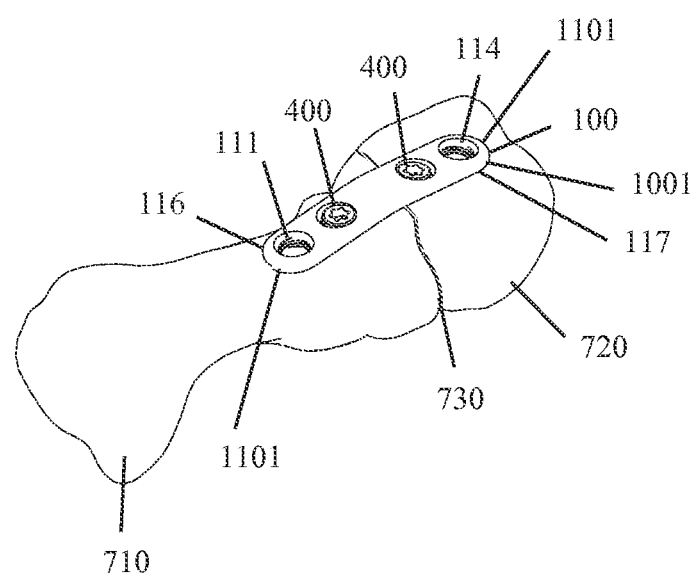
FIGS. 25-26 are perspective views illustrating the affixing of the shape memory plate to the first and second bones once the insertion tool is removed from the shape memory plate.

As illustrated in FIG. 22, once the first and second screws 400 have been screwed into the first bone 710 and the second bone 720, the two locating pins 300 are removed from the drill guide tubes 200, the platform 530 of the insertion tool 500, and the plate 100. The surgeon drills pilot holes through the drill guide tubes 200, through the platform 530 of the insertion tool 500, through respective screw holes 111 and 114 of the plate 100, and then into respective first and second bones 710 and 720 as shown in FIG. 23. Referring to FIG. 24, the remaining drill tubes 200 corresponding to screw holes 111 and 114 are removed from the plate 100 and the platform 530 of the insertion tool 500. The insertion tool 500 is then removed from the plate 100 as illustrated in FIG. 25.

Figure 26:
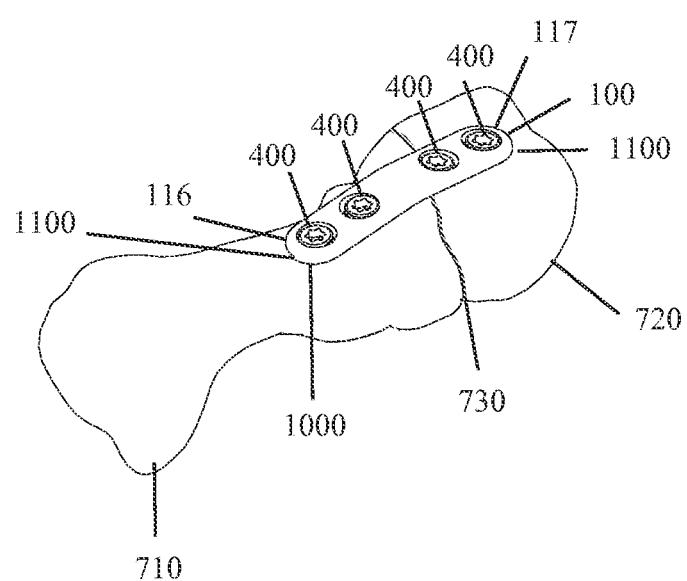
Figure 27:
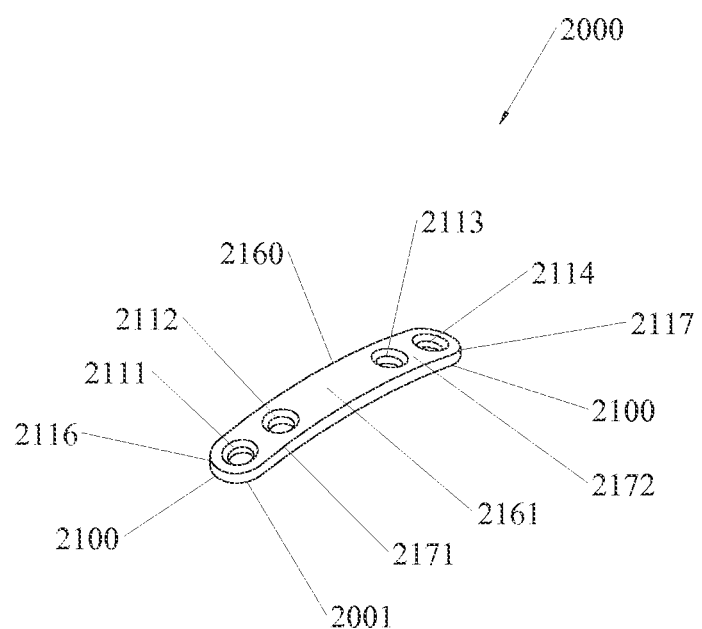
FIG. 27 is a perspective view of a shape memory plate in a first shape according to a second embodiment.
Figure 28:
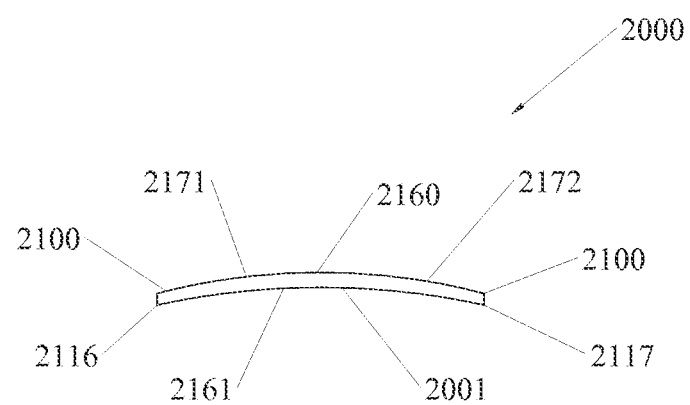
FIG. 28 is a front view of the shape memory plate in a first shape.
Figure 29:
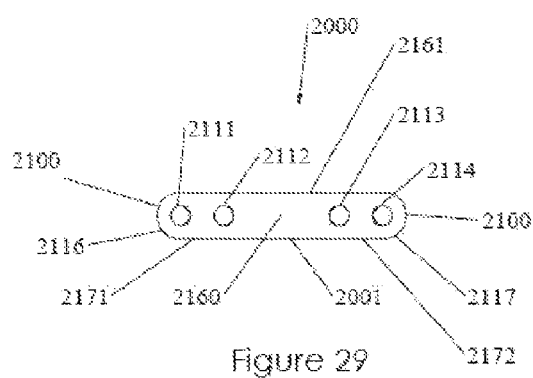
FIG. 29 is a bottom view of the shape memory plate in a first shape.
Figure 30:
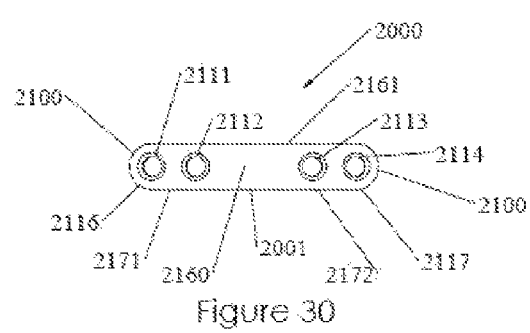
FIG. 30 is a top view of the shape memory plate in a first shape.
Figure 31:
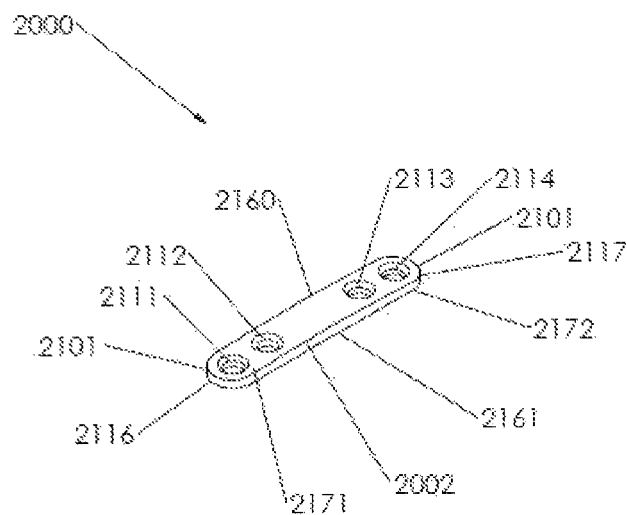
FIG. 31 is a perspective view of the shape memory plate in a second shape.
Figure 32:
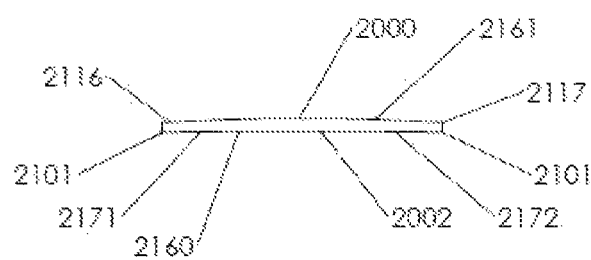
FIG. 32 is a front view of the shape memory plate in a second shape.

FIG. 26 illustrates the final step in the implantation of the plate 100 in the first bone 710 and the second bone 720. Third and fourth screws 400 respectively are screwed into the screw holes ill and 114 of the plate 100. The head threads 420 of the third and fourth screw 400 mate with the screw holes 111 and 114 of the plate 100 and the shank threads 410 of the screws 400 are screwed into the first bone 710 and the second bone 720. With the insertion tool 500 removed and the first, second, third, and fourth screws 400 secured with the plate 100 and the first and second bones 710 and 720, the shape memory plate 100 transforms from the second shape 1001 to the first implanted shape 1000. In particular, the end portions 116 and 117 move toward each other from the second position 1101 to the first position 1100 creating an arc in the body portion 160. Upon the transitioning of the plate 100 to the first implanted shape 1000, compression is created between the first bone 710 and the second bone 720 at the bone fusion location 730.

Summarizing the implantation, the surgeon selects a shape memory plate implant pre-loaded onto an insertion tool. The surgeon positions the plate at the juncture of two bones to be fused or fixated, and uses locating pins to temporarily hold the plate to the bones. The surgeon drills pilot holes into the bone. The surgeon then removes a first and second drill guide tube, replaces them with screws to keep the plate in place. The locating pins are removed and third and fourth pilot holes are drilled through the remaining drill guide tubes and into the bone. The surgeon removes the remaining drill guide tubes and replaces them with screws to secure the plate to the bone.

The ingenuity of this system is as follows. A shape memory plate that creates compression has to be held in a second insertion position until both sides of the plate are anchored in bone, lest the compressive force be released too early. This can be accomplished initially with an insertion tool that holds the plate in the second insertion position. However, the plate has to be anchored to the bone before the insertion tool can be removed to preserve the compressive force until the surgeon is ready. This then requires that the screws pass through the insertion tool in some way. The aforementioned method for implantation accomplishes these objectives. Furthermore, this method allows the surgeon to select the timing of the application of compressive force. A surgeon could potentially implant more than one plate, and leave the insertion tools in place, only to release them at the appropriate time. This sequence could allow more complex surgeries to take place. Furthermore, since the presence of the insertion tool can hide or obscure the visibility of the plate from the surgeon, the two locating pins insure that the plate remains properly oriented on the bones.

To use the plate 100, a medical device company or hospital could pre-load certain elements of the system prior to surgery. The plate 100 is moved from its first implanted shape 1000 shown in FIG. 1 to its second shape 1001 shown in FIG. 5. The plate 100 is held in its second shape 1001 via the drill guides tubes 200 and the insertion tool 500, which restrains the plate 100 in its second shape 1001. The plate 100 could be pre-loaded and delivered in a sterile package or, alternatively, the plate 100 shipped and prepared as described above before surgery.

FIGS. 27-32 illustrate an orthopedic plate 2000. The plate 2000 can be fabricated from a shape memory material such as nitinol (nickel-titanium), or any other elastic material capable of deforming and rebounding to an original shape. The plate 2000 includes a body portion 2160, screw holes 2111-2114, a central axis 2161, a first body section 2171 terminating in an end portion 2116, and a second body section 2172 terminating in an end portion 2117. One of ordinary skill in the art will recognize that the plate 2000 may include more or less screw holes depending upon the type of surgery. The screw holes 2111-2114, or a number of screw holes, can be smooth, tapered, or threaded as necessary to engage a screw. In the second embodiment, the screw holes 2111-2114 are shown with threads. The plate 2000 moves between a first implanted shape 2001 illustrated in FIGS. 1-4 and a second insertion shape 2002 illustrated in FIGS. 5 and 6. The first shape 2001 is the original fabrication shape of the plate 2000. In moving between the first implanted shape 2001 and the second insertion shape 2002, the end portions 2116 and 2117 move between a first position 2100 and a second position 2101.

In the second embodiment, the plate 2000 operates to create compression between first and second bones or bone parts. As such, the plate 2000 in the first shape 2001 has an arc in the body portion 2160 such that the end portions 2116 and 2117 in their first positions 2100 create compression between first and second bones or bone parts. In the second embodiment, the body portion 2160 of the plate 2000 in the second shape 2001 is substantially flat. However, the second shape 2002 of the plate 2000 may include an arc in the body portion 2160. In moving from the second shape 2002 to the first shape 2001, the end portions 2116 and 2117 move from the second position 2101 to the first position 2100 creating a more pronounced arc in the body portion 2160 between the second shape 2002 and the first shape 2001. One of ordinary skill the art will recognize that the amount of arc created in the body portion 2160 can be any amount that creates the desired compression.

The plate 2000 begins in the first shape 2001 and through application of an external force, the plate 2000 is moved from its first implantation shape 2001 to its second insertion shape 2002. In particular, the application of an external force causes the end portions 2116 and 2117 to bend away from each other, moving from the first position 2100 to the second position 2101 thereby substantially removing the arc from the body portion 2160 of the plate 2000.

The plate 2000 may change shape from the second shape 2002 to the first shape 2001 through the application of energy delivered from an external source such as room temperature, body temperature, or an external energy device. In the second embodiment however, the plate 2000 is superelastic in that the plate 2000 internally stores mechanical energy in its metallic structure when moved from its original first implantation shape 2001 to its second insertion shape 2002. The mechanical energy remains stored within the plate 2000 as the plate 2000 is held in the second shape 2002. Upon release the mechanical energy is recovered when the plate 2000 moves from the second shape 2002 to the first shape 2001. In moving from the from the second shape 2002 to the first shape 2001, the end portions 2116 and 2117 move from the second position 2101 to the first position 2100. In particular, in moving from the second position 2101 to the first position 2100, the end portions 2116 and 2117 contract reducing the distance between the end portions 2116 and 2117 and creating an arc in the body portion 2160 and the first and second body sections 21 71 and 2172. Furthermore,in moving between the second shape 2002 and the first shape 2001, the screw holes 2111-2114 can remain circular or change shape if it is desired that they bind upon screws.

Figure 33:
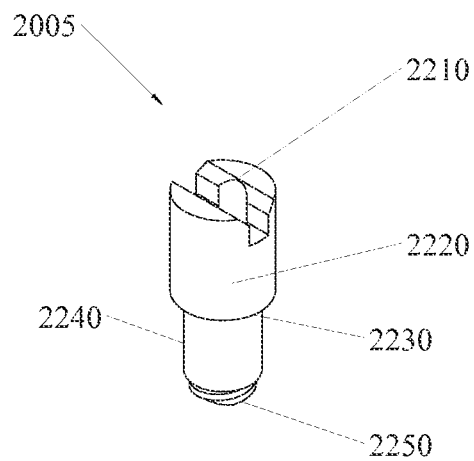
FIG. 33 is a perspective view of a drill guide tube.
Figure 34:
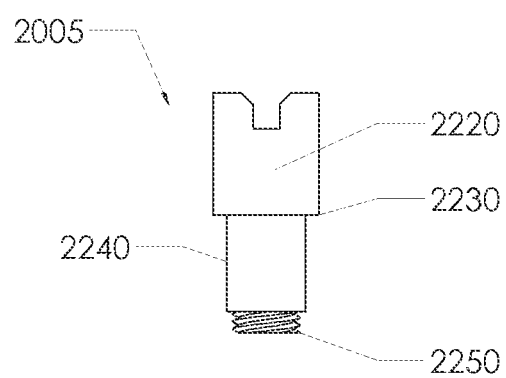
FIG. 34 is a front view of the drill guide tube.

FIGS. 33 and 34 illustrate a drill guide tube 2005. The drill guide tube 2005 can be made from metal or plate, and has an inner cannulation of diameter 2210 and an outer surface 2220. A shoulder 2230 is a location where a large outer surface 2220 reduces to a new small outer surface 2240 of smaller diameter. The screw threads 2250 extend from the small outer surface 2240, and are of the same thread characteristics needed to mate with the screw holes 2111-2114 of the plate 2000.

Figure 35:
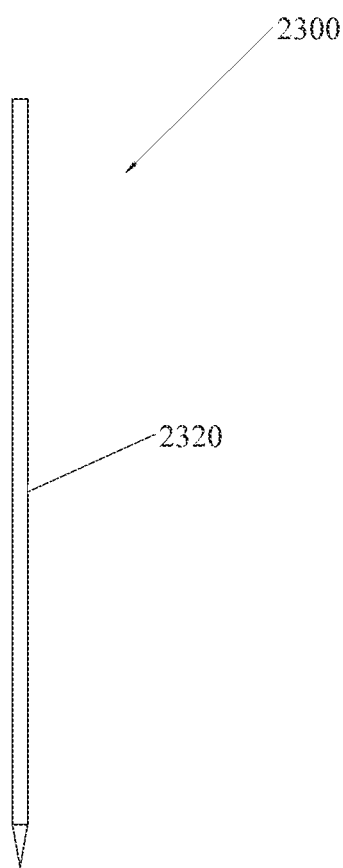
FIG. 35 is a perspective view of a locating pin.

FIG. 35 illustrates a locating pin 2300. The locating pin 2300 can be manufactured of any material; in the second embodiment, it is made from medical grade metal. A shank 2320 of the locating pin 2300 is of a diameter that will fit into the inner cannulation 2210 of the drill guide tube 2005. The locating pin 2300 holds the plate 2000 in a desired position so that a surgeon can drill holes into the patient's bone.

Figure 36:
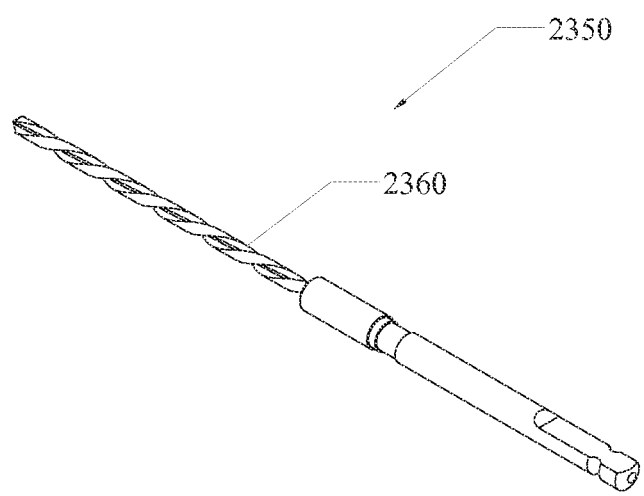
FIG. 36 is a perspective view of a drill bit.

FIG. 36 illustrates a drill bit 2350. The drill bit 2350 has cutting flutes 2360 for cutting through bone and can be manufactured of any material; in the second embodiment, it is made from medical grade metal. The drill bit 2350 is of a diameter that will fit into the inner cannulation 2210 of the drill guide tube 2005. The drill bit 2350 may include sizing lines to define certain depths for the drilling of a pilot hole.

Figure 37:
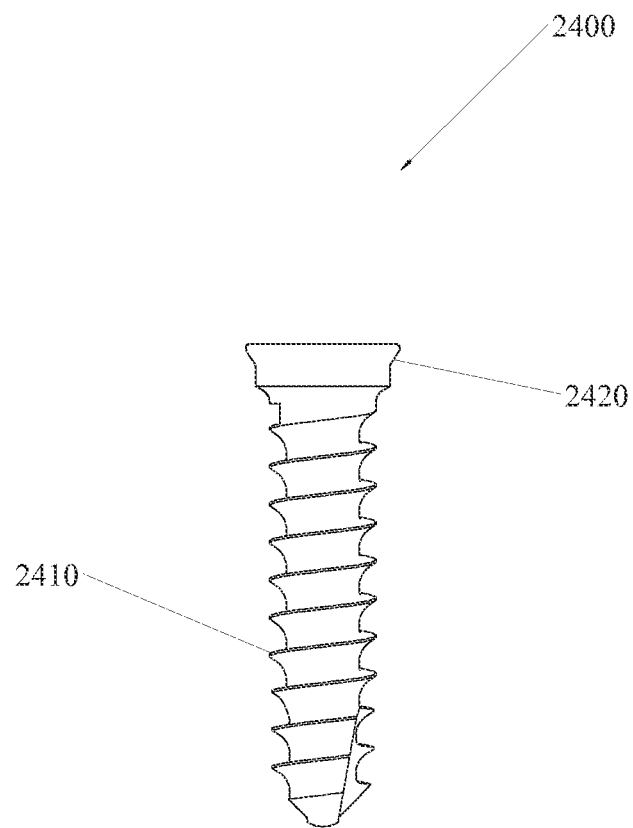
FIG. 37 is a front view of a screw.

FIG. 37 illustrates a screw 2400 designed to attach the plate 2000 to a bone. In the second embodiment, the screw 2400 has two threaded sections, shank threads 2410 and head threads 2420. The shank threads 2410 are designed to engage bone once inserted into a pilot hole created by the drill bit 2350. There is any number of thread characteristics related to pitch, diameter, and threads per inch that will accomplish this purpose. The head threads 2420 are designed to engage the screw holes 2111-2114 of the plate 2000.

Figure 38:
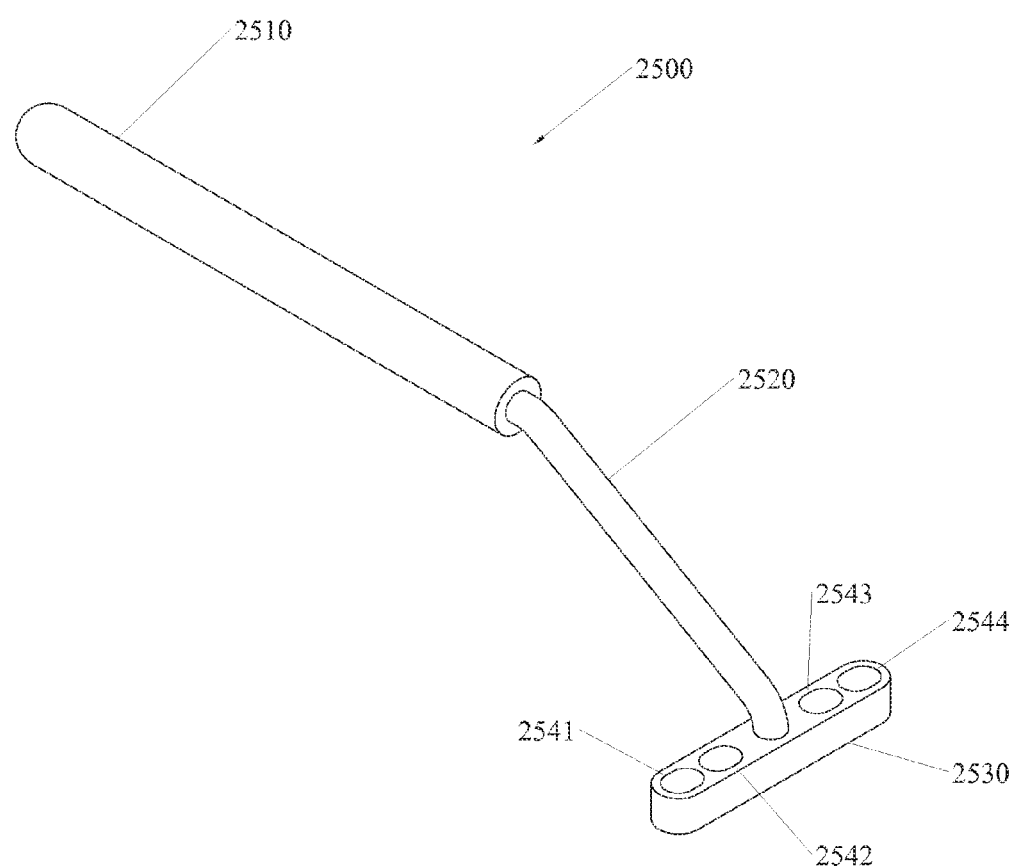
FIG. 38 is a perspective view of an insertion tool.
Figure 39:
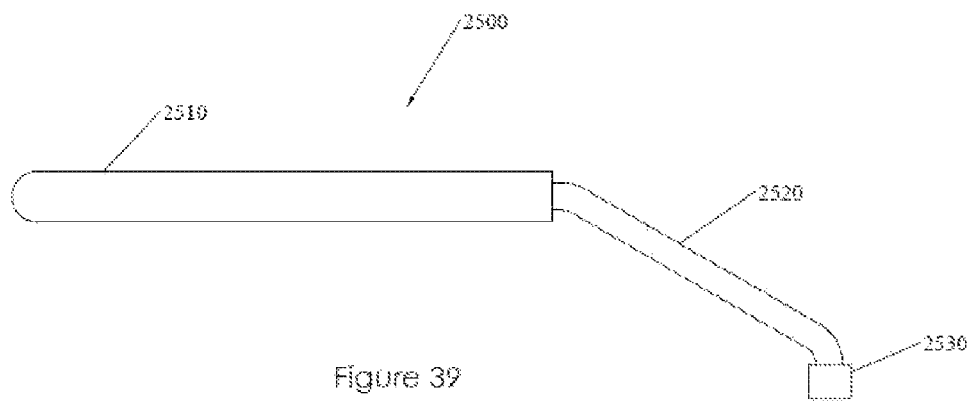
FIGS. 39 and 40 are side views of the insertion tool.
Figure 40:
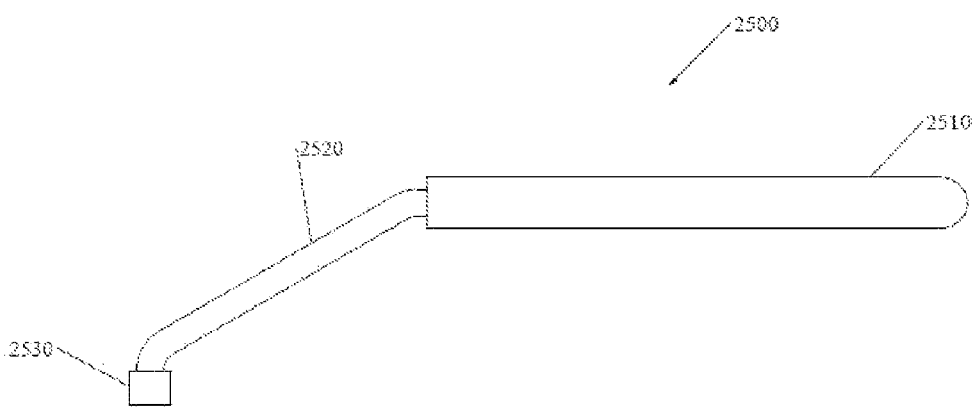
Figure 41:
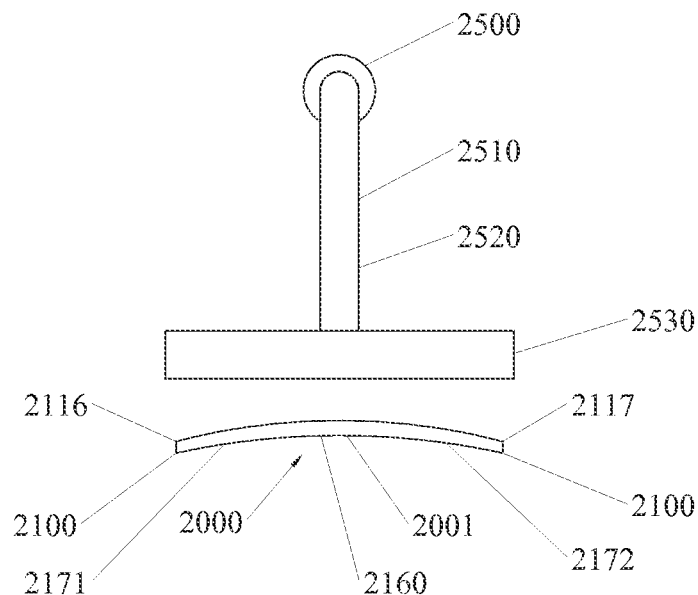
FIG. 41 is a front view of the insertion tool and the shape memory plate in the first position.
Figure 42:
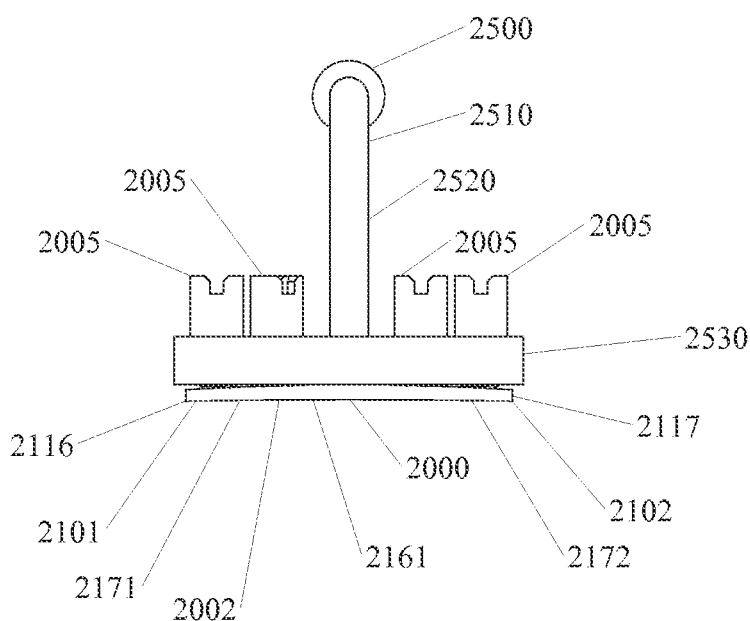
FIG. 42 is a front f the insertion tool and the shape memory plate in the second shape secured to the insertion tool using the drill guide tubes.
Figure 43:
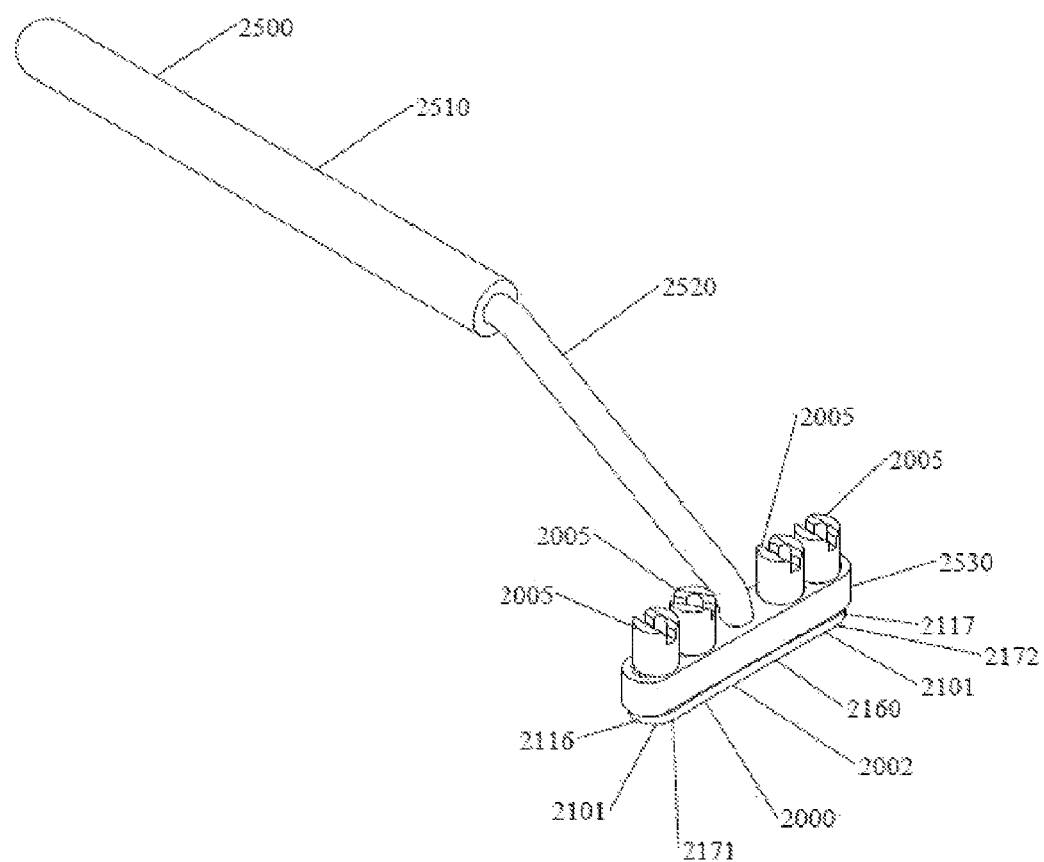
FIG. 43 is a perspective view of the insertion tool and the shape memory plate in the second shape secured to the insertion tool using the drill guide tubes.
Figure 44:
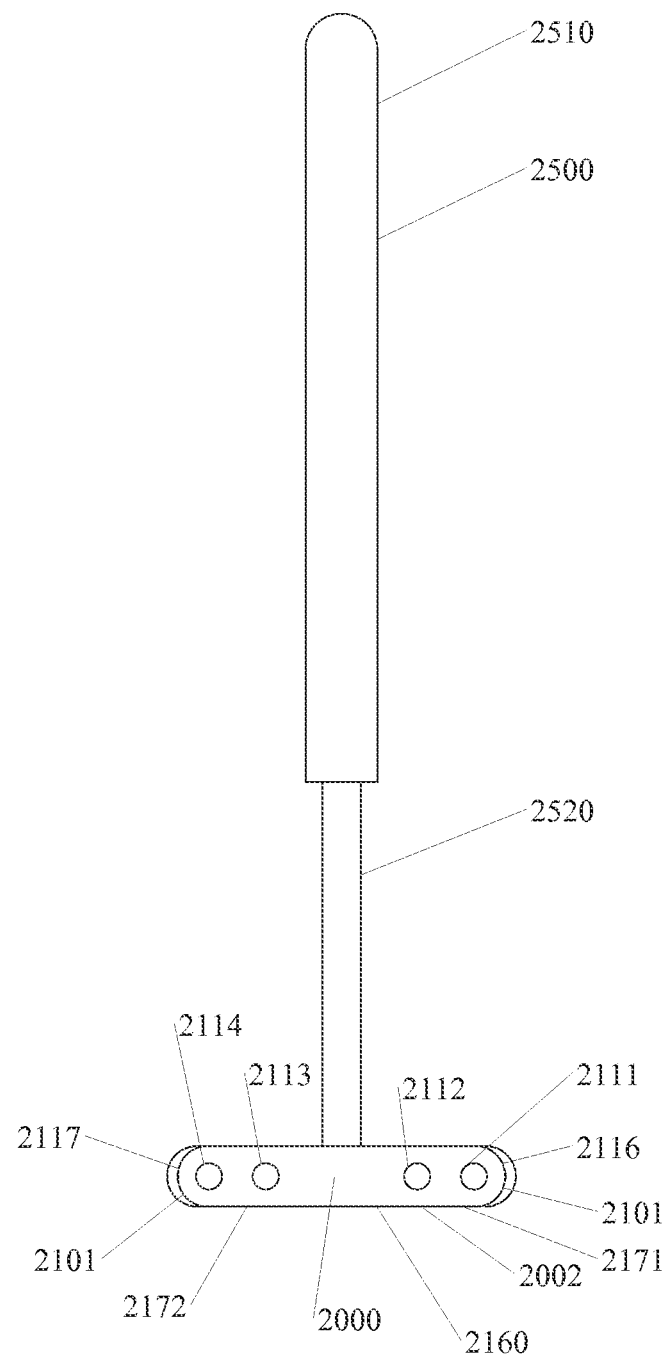
FIG. 44 is a bottom view of the insertion tool and the shape memory plate in the second shape secured to the insertion tool using the drill guide tubes.

FIGS. 38-40 illustrate an insertion tool 2500. The insertion tool 2500 consists of a handle 2510, a shaft 2520, and a platform 2530. The handle 2510 can be any shape such that it ergonomically fits a surgeon's hand. The shaft 2520 can be any length or angle as required to position the platform 2530 on a desired bone surface. In some applications, the shaft 2520 might not be needed at all, and could thus be eliminated from the insertion tool 2500. The platform 2530 is a solid material such as metal or plastic, designed to space drill guide holes 2541-2544 to the proper separation distance, as well as retain the plate 2000 in the second shape 2002. Thus, the drill guide holes 2541-2544 of the platform 2530 correspond to the separation distance of the screw holes 2111-2114 of the plate 2000 when it is in the second shape 2002. Although the second embodiment of the platform 2530 includes the drill guide holes 2541-2544, one of ordinary skill in the art will recognize that the screw holes 2541-2542 and the screw holes 2541-2542 respectively could be replaced with slots similar to the drill guide slot 541 and the drill guide slot 542 of the platform 530 according to the first embodiment.

FIGS. 41-44 illustrate an assembly showing the plate 2000, the four drill guide tubes 2005, and the insertion tool 2500. The plate 2000 begins in the first shape 2001 and ends in the second shape 2002 upon assembly with the insertion tool 2500. The body portion 2160 and the first and second body sections 2171 and 2172 of the plate 2000 mate with the platform 2530 of the insertion tool 2500. After mating with the platform 2530, the drill guide tubes 2005 are used secure the plate 2000 to the platform 2530 of the insertion tool 2500. In particular, the small outer surface 2240 of the drill guide tubes 2005 pass through the drill guide holes 2541-2544 that are located on the platform 2530 of the insertion tool 2500. The screw threads 2250 on the drill guide tubes 2200 are screwed into the screw holes 2111-2114 of the plate 2000 until the shoulders 2230 of the drill guide tubes 2005 abut the platform 2530 of the insertion tool 2500. In the second embodiment, the drill guide tubes 2005 screw into the screw holes 2112 and 2113 and then into the screw holes 2111 and 2114 thereby securing the plate 2000 to the platform 2530 of the insertion tool 2500. Once secured to the platform 2530 of the insertion tool 2500, the drill guide tubes 2005 maintain the plate 2000 in its second shape 2002. In mating the plate 2000 with the platform 2530, it may be necessary to first mechanically deform the plate 2000 from the first shape 2001 to the second shape 2002 before securing the plate 2000 with the platform 2530. Alternatively, securing the plate 2000 with the platform. 2530 using the drill guide tubes 2005 may facilitate the mechanical deformation of the plate 2005 from the first shape 2001 to the second shape 2002 without prior mechanical deformation.

Figure 45:
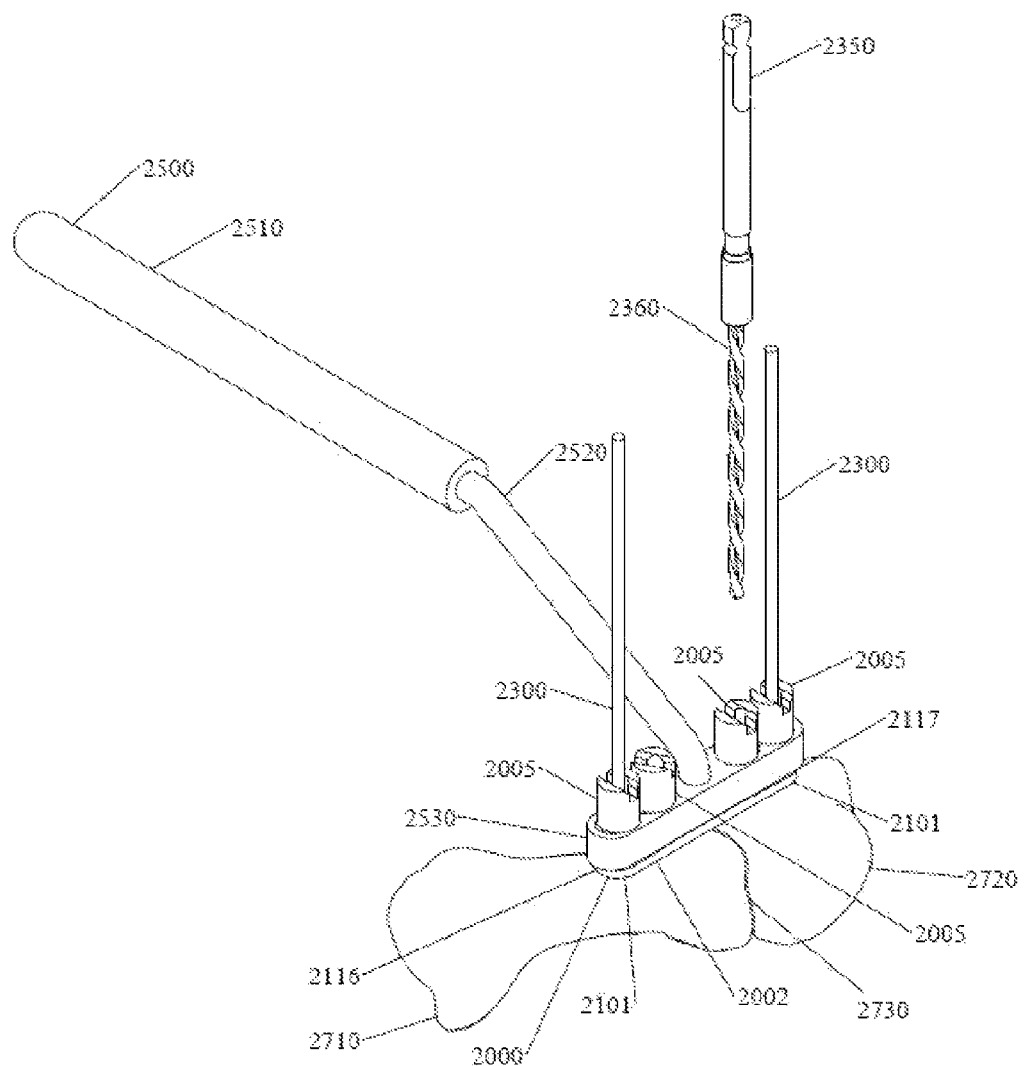
FIGS. 45-50 are perspective views illustrating the use of the insertion tool in affixing the shape memory plate to a first bone and a second bone.

FIGS. 45-52 illustrate a method of use for a shape memory plate 2000 to fixate two bones or bone fragments in a surgery. The surgical procedure begins with the surgeon trying to fixate a first bone 2710 and a second bone 2720. As illustrated in FIG. 45, the plate 2000 resides in the second shape 2002 as a result of the securing of the plate 2000 to the insertion tool 2500 using the drill guide tubes 2005 as described above. Using the insertion tool 2500, the plate 2000 is positioned on top of a bone fusion interface 2730, which lies between the first bone 2710 and the second bone 2720. The screw holes 2111-114 of the plate 2000 are positioned so that the screw holes 2111 and 2112 are over the first bone 2710 and screw hole 2113 and 2114 are over the second bone 2720.

After positioning the plate 2000, the surgeon uses two locating pins 2300 to temporarily anchor the plate 2000 in place. Specifically, the surgeon places the locating pins 2300 through the drill guide tubes 2005, through the platform 2530 of the insertion tool 2500, through respective screw holes 2111 and 2.11.4 of the plate 2000, and then into respective first and second bones 2710 and 2720. Once the plate 2000 is anchored in place, the surgeon drills pilot holes into the first and second bones 2710 and 2720 using the drill bit 2350. Specifically, the surgeon drills pilot holes through the drill guide tubes 2005, through the platform 2530 of the insertion tool 2500, through respective screw holes 2112 and 2113 of the plate 2000, and then into respective first and second bones 2710 and 2720. The surgeon can use any sizing lines located on the drill bit 2350 to assess the depth of a screw 2400 to anchor the plate 2000.

Figure 46:
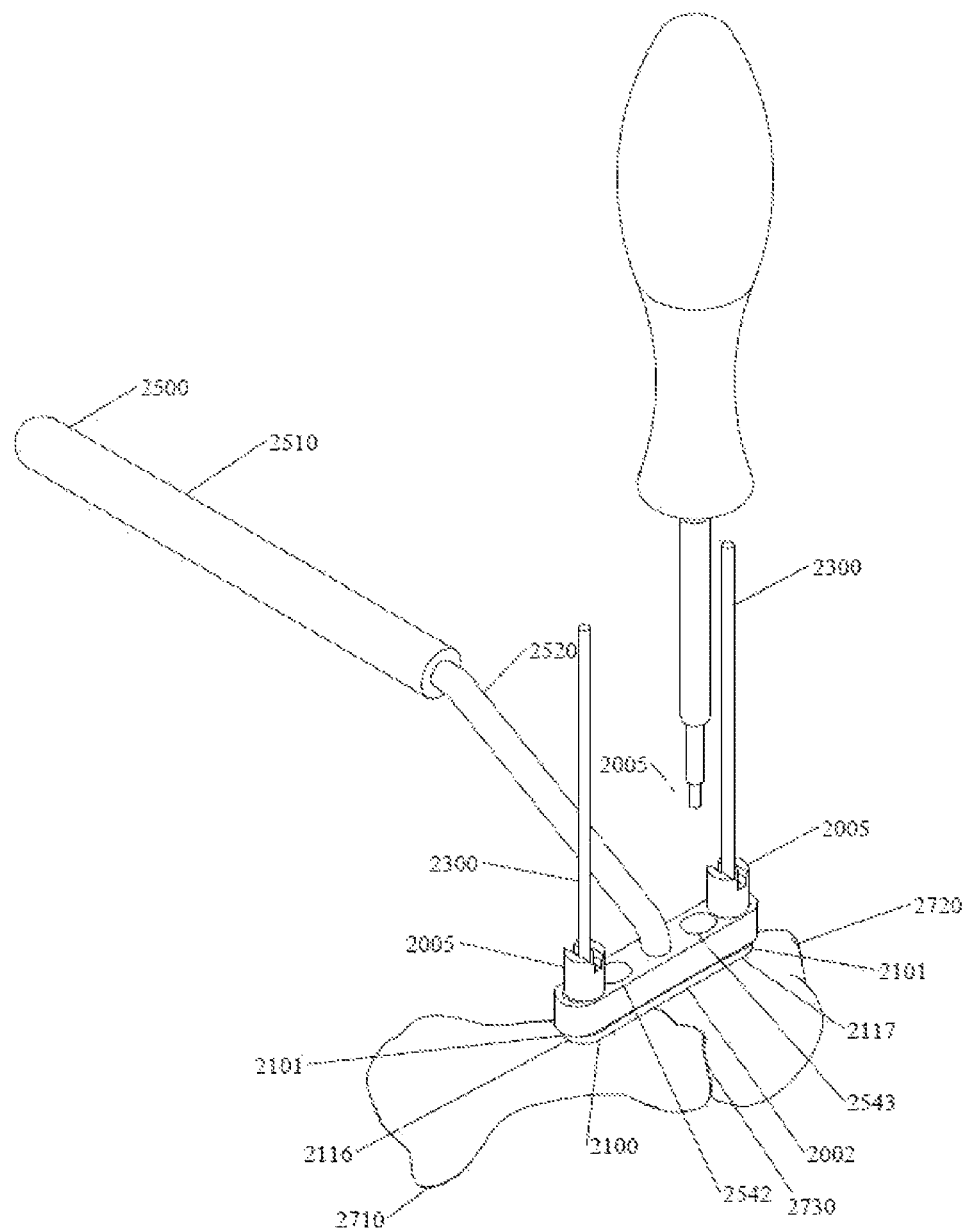
Figure 47:
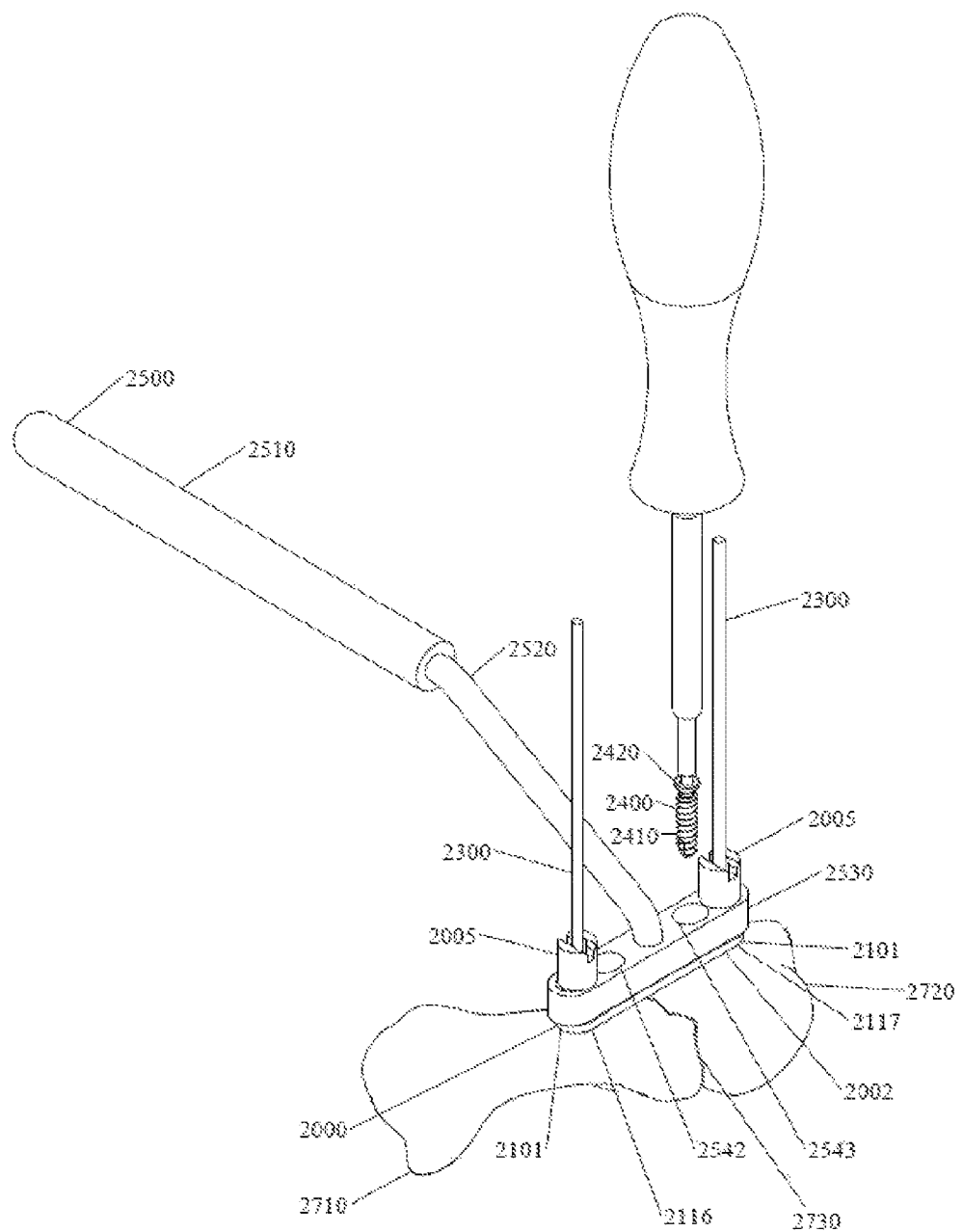

At this time, the surgeon is ready to screw the plate 2000 to the first and second bones 2710 and 2720. As illustrated in FIG. 46, the drill guide tubes 2005 corresponding to the screw holes 2112 and 2113 have been removed from the plate 2000 and the platform 2530 of the insertion tool 2500. Referring to FIG. 47, the surgeon then inserts first and second screws 2400 into the screw holes 2112 and 2113 of the plate 2000. To reach the screw holes 2112 and 2113, the first and second screws 2400 pass through the screw holes 2542 and 2543 of the insertion tool 2500. The head threads 2420 of the screws 2400 mate with the screw hole 2112 and 2113 of the plate 2000 and the shank threads 2410 of the screws 2400 are screwed into the first bone 2710 and the second bone 2720.

Figure 48:
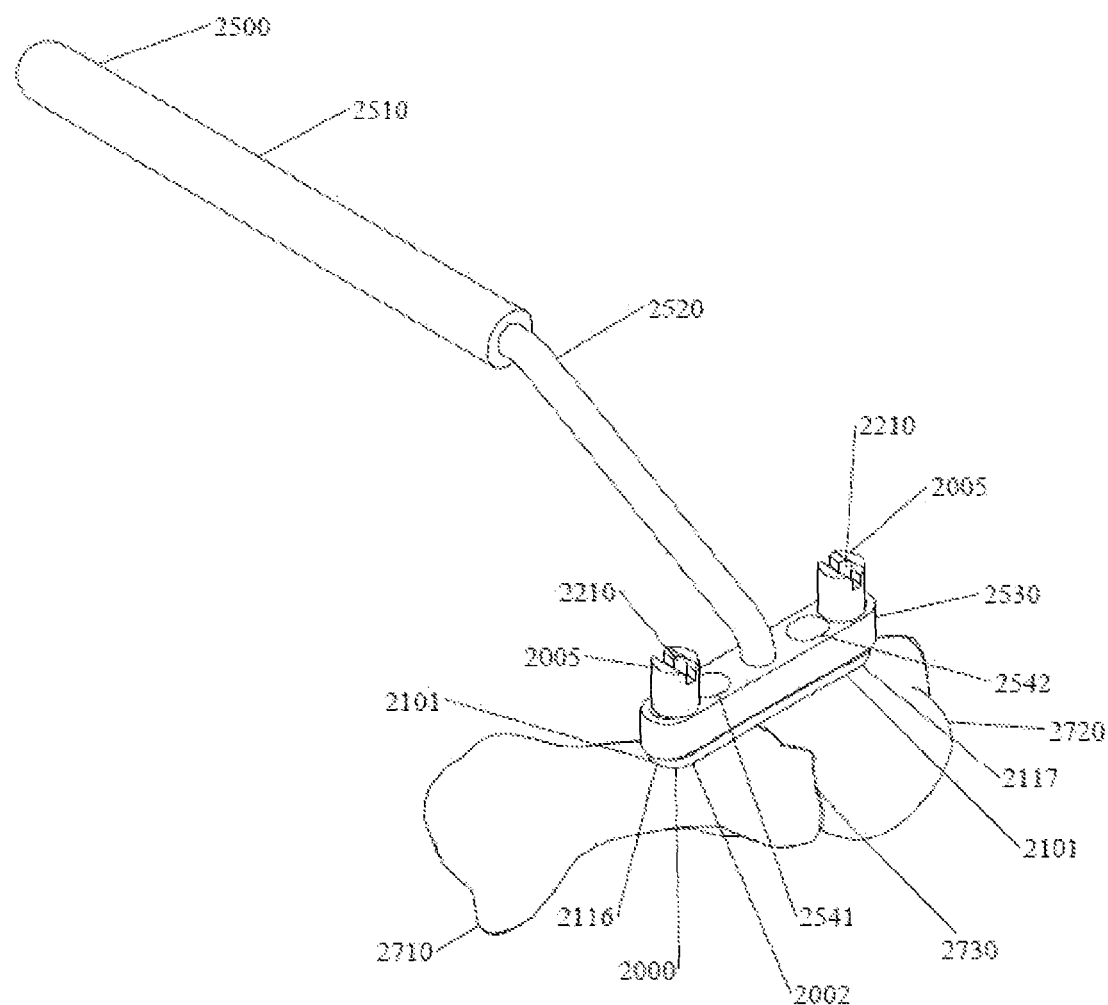
Figure 49:
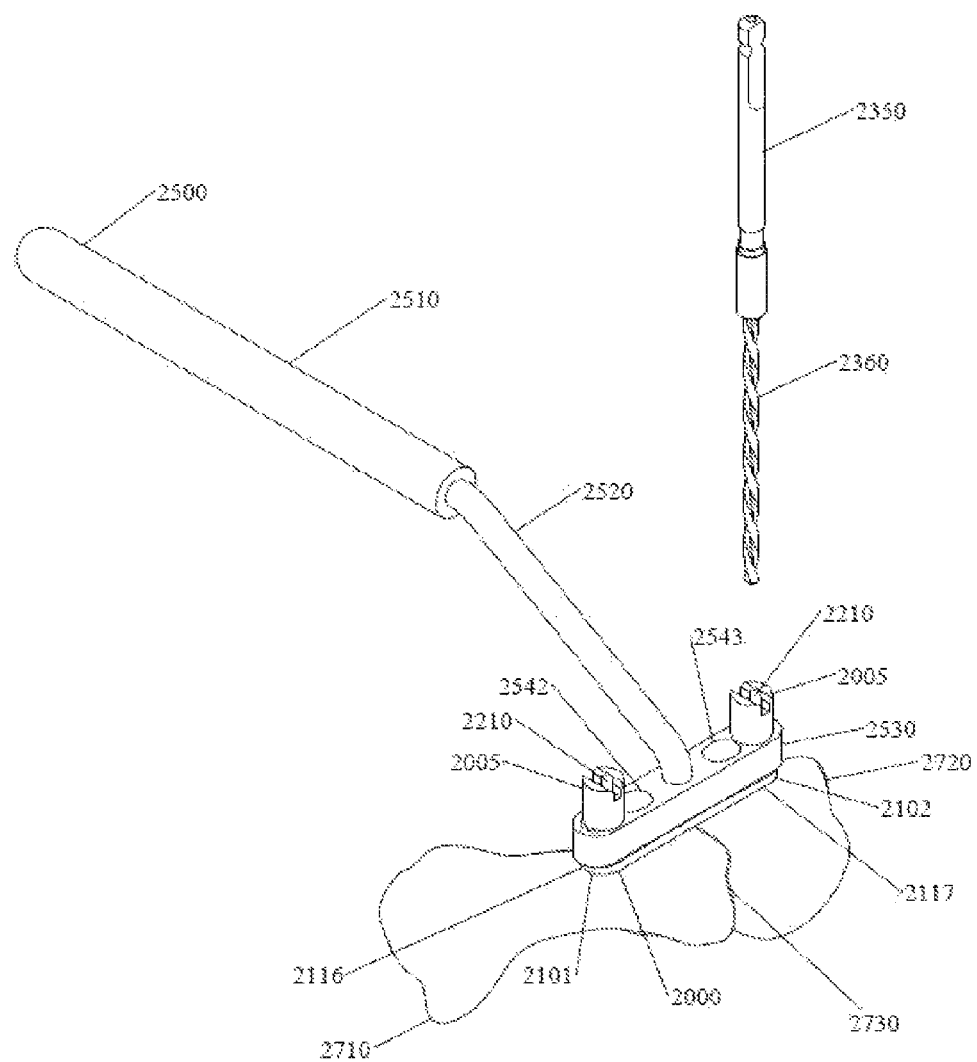
Figure 50:
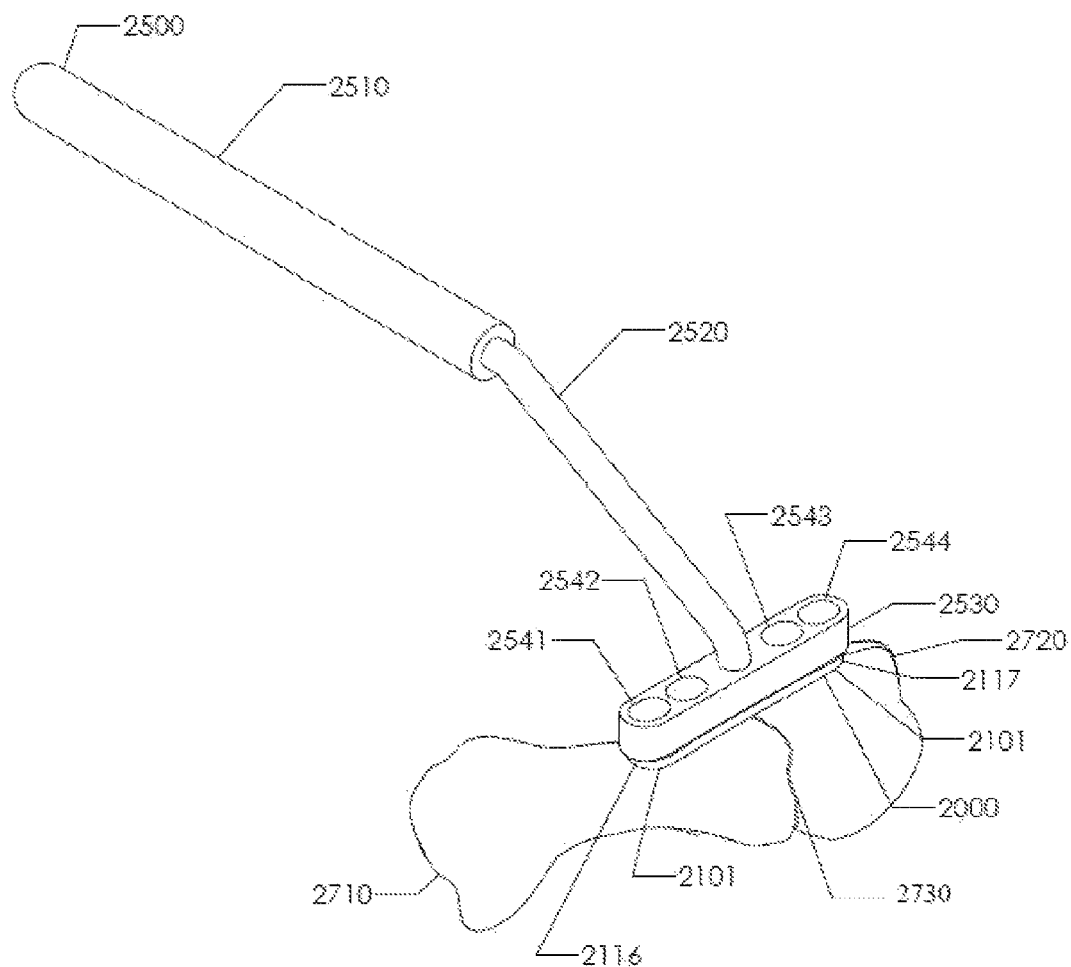
Figure 51:
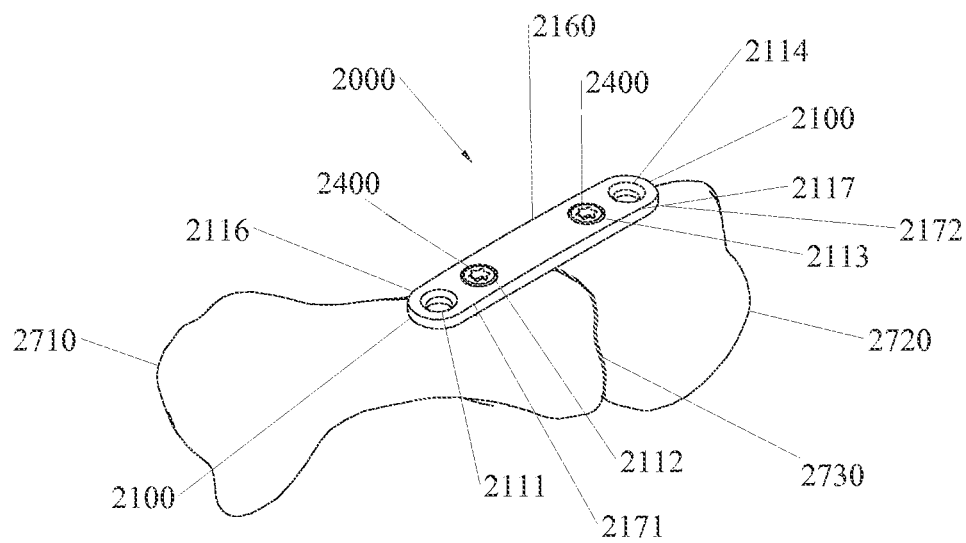
FIGS. 51-52 are perspective views illustrating the affixing of the shape memory plate to the first and second bones once the insertion tool is removed from the shape memory plate.

As illustrated in FIG. 48, once the first and second screws 2400 have been screwed into the first bone 2710 and the second bone 2720, the two locating pins 2300 are removed from the drill guide tubes 2005, the platform 2530 of the insertion tool 2500, and the plate 2000. The surgeon drills pilot holes through the drill guide tubes 2005, through the platform 2530 of the insertion tool 2500, through respective screw holes 2111 and 2114 of the plate 2000, and then into respective first and second bones 2710 and 2720 as shown in FIG. 49. Referring to FIG. 50, the remaining drill tubes 2005 corresponding to screw holes 2111 and 2114 are removed from the plate 2000 and the platform 2530 of the insertion tool 2500. The insertion tool 2500 is then removed from the plate 2000 as illustrated in FIG. 51.

Figure 52:
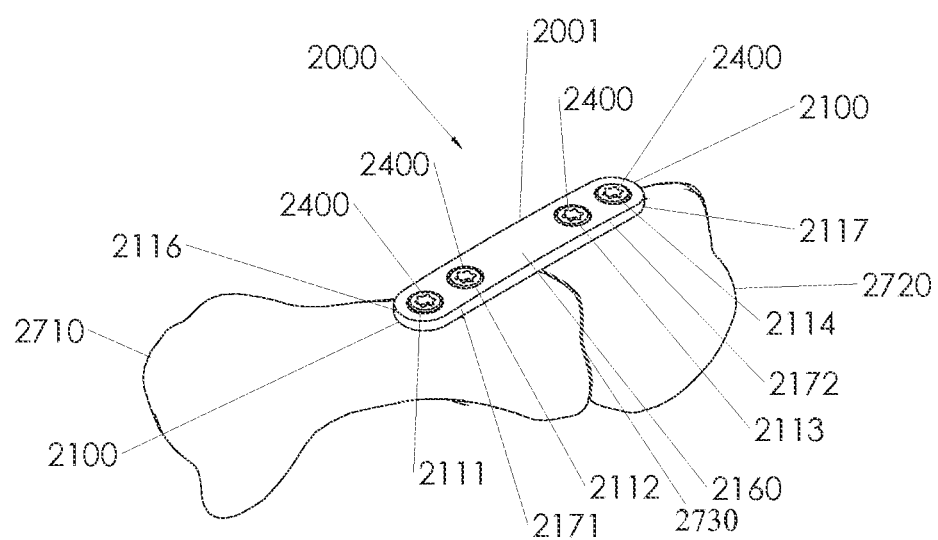

FIG. 52 illustrates the final step in the implantation of the plate 2000 in the first bone 2710 and the second bone 2720. Third and fourth screws 2400 respectively are screwed into the screw holes 2111 and 2114 of the plate 2000. To reach the screw holes 2111 and 2114, the third and fourth screws 2400 pass through the screw holes 2541 and 2544 of the insertion tool 2500. The head threads 2420 of the third and fourth screw 2400 mate with the screw holes 2111 and 2114 of the plate 2000 and the shank threads 2410 of the screws 2400 are screwed into the first bone 2710 and the second bone 2720. With the insertion tool 2500 removed and the first, second, third, and fourth screws 2400 secured with the plate 2000 and the first and second bones 2710 and 2720, the shape memory plate 2000 transforms from the second shape 2002 to the first shape 2001. In particular, the end portions 2116 and 2117 move toward each other from the second position 2101 to the first position 2100 creating an arc in the body portion 2160. Upon the transitioning of the plate 2100 to the first shape 2001, compression is created between the first bone 2710 and the second bone 2720 at the bone fusion location 2730.

Summarizing the implantation, the surgeon selects a shape memory plate implant pre-loaded onto an insertion tool. The surgeon positions the plate at the juncture of two bones to be fused or fixated, and uses locating pins to temporarily hold the plate to the bones. The surgeon drills pilot holes into the bone. The surgeon then removes a first and second drill guide tube, replaces them with screws to keep the plate place. The locating pins are removed and third and fourth pilot holes are drilled through the remaining drill guide tubes and into the bone. The surgeon removes the remaining drill guide tubes and replaces them with screws to secure the plate to the bone.

The ingenuity of this system is as follows. A shape memory plate that creates compression has to be held in a second insertion position until both sides of the plate are anchored in bone, lest the compressive force be released too early. This can be accomplished initially with an insertion tool that holds the plate in the second insertion position. However, the plate has to be anchored to the bone before the insertion tool can be removed to preserve the compressive force until the surgeon is ready. This then requires that the screws pass through the insertion tool in some way. The aforementioned method for implantation accomplishes these objectives. Furthermore, this method allows the surgeon to select the timing of the application of compressive force. A surgeon could potentially implant more than one plate, and leave the insertion tools in place, only to release them at the appropriate time. This sequence could allow more complex surgeries to take place. Furthermore, since the presence of the insertion tool can hide or obscure the visibility of the plate from the surgeon, the two locating pins insure that the plate remains properly oriented on the bones.

To use the plate 2000, a medical device company or hospital could pre-load certain elements of the system prior to surgery. The plate 2000 is moved from its first implantation shape 2001 shown in FIG. 27 to its second insertion shape 2002 shown in FIG. 31. The plate 2000 is held in its second shape 2002 via the drill guides tubes 2005 and the insertion tool 2500, which restrains the plate 2000 in its second shape 2002. The plate 2000 could be pre-loaded and delivered in a sterile package or, alternatively, the plate 2000 shipped and prepared as described above before surgery.

Although the present invention has been described in terms of the foregoing preferred embodiments, such description has been fir exemplary purposes only and, as will be apparent to those of ordinary skill in the art, many alternatives, equivalents, and variations of varying degrees will fall within the scope of the present invention. That scope, accordingly, is not to be limited in any respect by the foregoing detailed description; rather,it is defined only by the claims that follow.

The invention claimed is:

1. A fixation system, comprising:
    a plate movable between an implantation shape and an insertion shape such that the plate creates compression between a first bone and a second bone, the plate, comprising:
        a body portion having a central axis,
        a first body section extending from the body portion and terminating in a first end portion,
        a second body section extending from the body portion and terminating in a second end portion,
        first and second screw holes disposed in the first body section, and
        third and fourth screw holes disposed in the second body section;
    an insertion tool adapted to hold the plate in the insertion shape, wherein the insertion tool allows locating of the plate in the insertion shape for affixing with the first bone and the second bone, further wherein release of the plate from the insertion tool after affixation of the plate with the first bone and the second bone allows the plate to move from its insertion shape to its implantation shape, thereby compressing the first bone with the second bone, the insertion tool comprising:
        a platform adapted to mate with the body portion and the first and second body sections of the plate, wherein the platform includes a first slot that aligns with the first and second screw holes of the plate and a second slot that aligns with the third and fourth screw holes of the plate; and
    first, second, third, and fourth drill guide tubes each including an inner cannulation adapted to receive a locating pin or a drill bit, wherein the first and second drill guide tubes insert within the first slot of the platform and mate respectively with the first and second screw holes of the plate and the third and fourth drill guide tubes insert within the second slot of the platform and mate respectively with the third and fourth screw holes of the plate such that the platform holds the plate in the insertion shape.

2. The fixation system according to claim 1, wherein the first end portion and the second end portion have a first linear distance when the plate is in the implantation shape and a second linear distance when the plate is in the insertion shape, further wherein the first linear distance is less than the second linear distance such that plate creates compression during movement of the plate from the insertion shape toward the implantation shape.

3. The fixation system according to claim 2, wherein the first body section and the second body section rotate about the central axis of the body portion during movement of the plate between the insertion shape and the implantation shape.

4. The fixation system according to claim 1, further comprising:
    a first and second locating pins adapted to temporarily anchor the plate with the first and second bones;
    the first locating pin insertable through one of the first and second drill guide tubes and one of the first and second screw holes of the plate wherein the first locating pin retains the plate at the first bone; and
    the second locating pin inserts through one of the third and fourth drill guide tubes and one of the third and fourth screw holes of the plate wherein the second locating pin retains the plate at the second bone.

5. The fixation system according to claim 1, wherein the insertion tool further comprises a shaft secured with the platform.

6. The fixation system according to claim 1, further comprising:
    a drill bit adapted to create a hole in the first and second bone, wherein the drill bit inserts through one of the first, second, third, and fourth drill guide tubes and through one of the first and second screw hole of the plate, further wherein the drill bit produces a drill hole in one of the first and second bones.

7. The fixation system according to claim 1, wherein:
    the first, second, third, and fourth screw holes include threads, wherein the threads engage a respective one of the first, second, third, and fourth drill guide tubes to maintain the first, second, third, and fourth drill guide tubes secured to the plate with the platform therebetween, further wherein, after removal of the first, second, third, and fourth drill guide tubes, the threads engage a screw inserted into the first or second bones to maintain the plate secured with the first and second bones.

8. The fixation system according to claim 1, further comprising a package adapted to receive therein the plate coupled with the insertion tool such that the insertion tool retains the plate in its insertion position.

9. The fixation system according to claim 8, wherein the package maintains the plate and the insertion tool sterile after sterilization of the fixation system.

10. The fixation system according to claim 9, further comprising a package adapted to receive therein the plate coupled with the insertion tool such that the insertion tool retains the plate in its insertion position and the first, second, third, and fourth drill guide tubes coupled with the plate.

11. The fixation system according to claim 10, wherein the package maintains the plate, the insertion tool, and the first, second, third, and fourth drill guide tubes sterile after sterilization of the fixation system.

12. A method for affixing a first bone with a second bone, comprising:
 1) providing a fixation system, comprising:
  a plate movable between an implantation shape and an insertion shape such that the plate creates compression between a first bone and a second bone,
  an insertion tool adapted to hold the plate in the insertion shape, and
  first, second, third, and fourth drill guide tubes insertable through the insertion tool and securable to the plate with the insertion tool disposed therebetween such that the insertion tool holds the plate in the insertion shape;
 2) placing the fixation system onto the first and second bones;
 3) inserting a first locating pin through the first drill guide tube and into the first bone and a second locating pin through the fourth drill guide tube and into the second bone to retain the fixation system on the first and second bones;
 4) inserting a drill bit through the second drill guide tube and drilling a hole into the first bone;
 5) inserting a drill bit through the third drill guide tube and drilling a hole into the second bone;
 6) removing the second drill guide tube from the plate;
 7) inserting a first screw through the insertion tool and securing the first screw with the plate and the first bone;
 8) removing the third drill guide tube from the plate;
 9) inserting a second screw through the insertion tool and securing the second screw with the plate and the second bone;
 10) removing the first locating pin from the first drill guide tube and the second locating pin from the fourth drill guide tube;
 11) inserting a drill bit through the first drill guide tube and drilling a hole into the first bone;
 12) inserting a drill bit through the fourth drill guide tube and drilling a hole into the second bone;
 13) removing the first and fourth drill guide tubes from the plate;
 14) decoupling the insertion tool from the plate;
 15) securing a third screw with the plate and the first bone;
 16) securing a fourth screw with the plate and the second bone; and
 17) the plate moves from the insertion shape to the implantation shape, thereby compressing the first bone and the second bone.

13. A method for affixing a first bone with a second bone, comprising:
 1) providing a first fixation system, comprising:
  a plate movable between an implantation shape and an insertion shape such that the plate creates compression between a first bone and a second bone,
  an insertion tool adapted to hold the plate in the insertion shape, and
  first, second, third, and fourth drill guide tubes insertable through the insertion tool and securable to the plate with the insertion tool disposed therebetween such that the insertion tool holds the plate in the insertion shape;
 2) providing a second fixation system, comprising:
  a plate movable between an implantation shape and an insertion shape such that the plate creates compression between a first bone and a second bone,
  an insertion tool adapted to hold the plate in the insertion shape, and first, second, third, and fourth drill guide tubes insertable through the insertion tool and securable to the plate with the insertion tool disposed therebetween such that the insertion tool holds the plate in the insertion shape;
 3) placing the first fixation system onto the first and second bones;
 4) inserting a first locating pin through the first drill guide tube of the first fixation system and into the first bone and a second locating pin through the fourth drill guide tube of the first fixation system and into the second bone to retain the first fixation system on the first and second bones;
 5) inserting a drill bit through the second drill guide tube of the first fixation system and drilling a hole into the first bone;
 6) inserting a drill bit through the third drill guide tube of the first fixation system and drilling a hole into the second bone;
 7) removing the second drill guide tube of the first fixation system from the plate of the first fixation system;
 8) inserting a first screw through the insertion tool of the first fixation system and securing the first screw with the plate of the first fixation system and the first bone;
 9) removing the third drill guide tube of the first fixation system from the plate of the first fixation system;
 10) inserting a second screw through the insertion tool of the first fixation system and securing the second screw with the plate of the first fixation system and the second bone;
 11) removing the first locating pin from the first drill guide tube of the first fixation system and the second locating pin from the fourth drill guide tube of the first fixation system;
 12) inserting a drill bit through the first drill guide tube of the first fixation system and drilling a hole into the first bone;
 13) inserting a drill bit through the fourth drill guide tube of the first fixation system and drilling a hole into the second bone;
 14) removing the first and fourth drill guide tubes of the first fixation system from the plate of the first fixation system;
 15) securing a third screw with the plate of the first fixation system and the first bone;

16) securing a fourth screw with the plate of the first fixation system and the second bone;
17) placing the second fixation system onto the first and second bones;
18) inserting a first locating pin through the first drill guide tube of the second fixation system and into the first bone and a second locating pin through the fourth drill guide tube of the second fixation system and into the second bone to retain the second fixation system on the first and second bones;
19) inserting a drill bit through the second drill guide tube of the second fixation system and drilling a hole into the first bone;
20) inserting a drill bit through the third drill guide tube of the second fixation system and drilling a hole into the second bone;
21) removing the second drill guide tube of the second fixation system from the plate of the second fixation system;
22) inserting a first screw through the insertion tool of the second fixation system and securing the first screw with the plate of the second fixation system and the first bone;
23) removing the third drill guide tube of the second fixation system from the plate of the second fixation system;
24) inserting a second screw through the insertion tool of the second fixation system and securing the second screw with the plate of the second fixation system and the second bone;
25) removing the first locating pin from the first drill guide tube of the second fixation system and the second locating pin from the fourth drill guide tube of the second fixation system;
26) inserting a drill bit through the first drill guide tube of the second fixation system and drilling a hole into the first bone;
27) inserting a drill bit through the fourth drill guide tube of the second fixation system and drilling a hole into the second bone;
28) removing the first and fourth drill guide tubes of the second fixation system from the plate of the second fixation system;
29) securing a third screw with the plate of the second fixation system and the first bone;
30) securing a fourth screw with the plate of the second fixation system and the second bone;
31) decoupling the insertion tool of the first fixation system from the plate of the first fixation system and the insertion tool of the second fixation system from the plate of the second fixation system; and
32) the plates of the first and second fixation systems move from the insertion shape to the implantation shape, thereby compressing the first bone and the second bone.

* * * * *